(12) United States Patent
Pomper et al.

(10) Patent No.: US 8,778,304 B2
(45) Date of Patent: Jul. 15, 2014

(54) TSPO-TARGETING COMPOUNDS AND USES THEREOF

(75) Inventors: Martin G. Pomper, Baltimore, MD (US); Haofan Wang, Baltimore, MD (US); Tomas R. Guilarte, New York, NY (US)

(73) Assignee: The Johns Hopkins University, Baltimore, MD (US)

( * ) Notice: Subject to any disclaimer, the term of this patent is extended or adjusted under 35 U.S.C. 154(b) by 330 days.

(21) Appl. No.: 13/034,320

(22) Filed: Feb. 24, 2011

(65) Prior Publication Data

US 2011/0212025 A1    Sep. 1, 2011

Related U.S. Application Data

(60) Provisional application No. 61/307,557, filed on Feb. 24, 2010.

(51) Int. Cl.
*A61K 51/00* (2006.01)
*A61K 49/00* (2006.01)

(52) U.S. Cl.
USPC ........... 424/1.81; 424/1.65; 424/9.1; 424/9.3; 424/9.4

(58) Field of Classification Search
USPC ............ 424/1.65, 9.3, 9.4, 1.81, 9.1; 544/281
See application file for complete search history.

(56) References Cited

U.S. PATENT DOCUMENTS

2009/0311176 A1    12/2009    Kassiou et al.

FOREIGN PATENT DOCUMENTS

| AU | 2007/252273 A1 | 11/2007 |
|---|---|---|
| WO | WO-2007/134362 A1 | 11/2007 |
| WO | WO-2009/004621 A1 | 1/2009 |
| WO | WO-2009/079683 A1 | 7/2009 |

OTHER PUBLICATIONS

Haofan Wang et al., Synthesis of [125I] iodoDPA-713: A new probe for imaging inflammation, Biochemical and Biophysical Research Communication, 389, 80-83, 2009.*
Banati et al., Brain, vol. 123, No. 11, pp. 2321-2337, 2000.
Boutin et al., J. Nucl. Med., vol. 48, No. 4, pp. 573-581, 2007.
Cagnin et al., Lancet, vol. 358, No. 9280, pp. 461-467, 2001.
Cagnin et al., Neurotherapeutics, vol. 4, pp. 443-452, 2007.
Chauveau et al., J. Nucl. Med., vol. 50, pp. 468-476, 2009.
Chen et al., Brain, vol. 127, No. 6, pp. 1379-1392, 2004.
Chen et al., Pharmacol. Ther., vol. 118, pp. 1-17, 2008.
Chen et al., Toxicol. Sci., vol. 91, No. 2, pp. 532-539, 2006.
Cosenza-Nashat et al., Neuropathol. Applied Neurobiol., vol. 35, No. 3, pp. 306-328, 2009.
Damont et al. (2008) Radiosynthesis of [18F]DPA-714, a selective radioligand for imaging the translocator protein (18 kDa) with PET.
Journal of Labelled Compounds and Radiopharmaceuticals, 51(7), 286-292.
Doorduin et al., Mol. Imag. Biol., vol. 11, No. 6, pp. 386-398, 2009.
Endres et al., J. Nucl. Med., vol. 50, No. 8, pp. 1276-1282, 2009.
Gerhard et al., Neurobiol. Dis., vol. 21, No. 2, pp. 404-412, 2006.
Gerhard et al., NeuroImage, vol. 24, No. 2, pp. 591-595, 2005.
Gerhard et al., Neuroreport., vol. 11 No. 13, pp. 2957-2960, 2000.
Guilarte et al., Neuroscience, vol. 122, No. 2, pp. 499-513, 2003.
Guilarte et al., Neurotoxicology, vol. 16, No. 3, pp. 441-450, 1995.
Huang et al., Hum. Mol. Genet., vol. 6, No. 11, pp. 1879-1885, 1997.
James ML, Selleri S, Kassiou M. Development of ligands for the peripheral benzodiazepine receptor. Curr Med Chem. 2006;13(17):1991-2001.
James, M. L., Fulton, R. R., Henderson, D. J., Eberl, S., Meikle, S. R., Thomson, S., et al. (2005). Synthesis and in vivo evaluation of a novel peripheral benzodiazepine receptor PET radioligand. Bioorganic and Medicinal Chemistry, 13(22), 6188-6194. Retrieved from www.scopus.com <http://www.scopus.com>.
James, M. L., Fulton, R. R., Vercoullie, J., Henderson, D. J., Garreau, L., Chalon, S., et al. (2008). DPA-714, a new translocator protein-specific ligand: Synthesis, radiofluorination, and pharmacologic characterization. Journal of Nuclear Medicine, 49(5), 814-822.
Jeyakumar et al., Ann. Neurol., vol. 56, No. 5, pp. 642-649, 2004.
Jeyakumar et al., Neuropathol. Applied Neurobiol., vol. 28, No. 5, pp. 343-357, 2002.
Kuhlmann et al. Toxicol. Sci., vol. 48, No. 1, pp. 107-116, 1999.
Kuhlmann et al., Brain Research, vol. 751, No. 2, pp. 281-288, 1997.
Kuhlmann et al., J. Neurochem., vol. 74, No. 4, pp. 1694-1704, 2000.
Lucignani, G. (2007). Rubor, calor, tumor, dolor, functio laesa . . . or molecular imaging. European Journal of Nuclear Medicine and Molecular Imaging, 34(12), 2135-2141.
Maeda et al., Brain Res., vol. 1157, pp. 100-111, 2007.
Maegawa et al., Pediatrics, vol. 118, No. 5, pp. e1550-1562, 2006.
Meikle et al., Phys. Med. Biol., vol. 50, No. 22, pp. R45-R61, 2005.
Miyazawa et al., Acta Neurochir., vol. 137, No. 3-4, pp. 207-216, 1995.
Ouchi et al., Ann. Neurol., vol. 57, No. 2, pp. 168-175, 2005.
Papadopoulos et al., Exp. Neurol., vol. 219, No. 1, pp. 53-57, 2009.
Pappata et al. Neurology, vol. 55, No. 7, pp. 1052-1054, 2000.
Price et a., Stroke, vol. 37, No. 7, pp. 1749-1753, 2006.
Rao et al., Exp. Neurol., vol. 161, No. 1, pp. 102-114, 2000.
Roberts, J. C., Friel, S. L, Roman, S., Perren, M., Harper, A., Davis, J. B., et al. (2009). Autoradiographical imaging of PPARy agonist effects on PBR/TSPO binding in TASTPM mice. Experimental Neurology, 216(2), 459-470.
Sango et al., "Mouse models of Tay-Sachs and Sandhoff diseases differ in neurologic phenotype and ganglioside metabolism," Nature Genetics, vol. 11, No. 2, pp. 170-176, 1995.
Scarf et al., J. Med. Chem., vol. 52, pp. 581-592, 2009.
Szarka et al., "A murine model of pulmonary damage induced by lipopolysaccharide via intranasal instillation," J. Immunol. Methods, vol. 202, pp. 49-57, 1997.
Tai et al., Brain, vol. 130, No. 7, pp. 1759-1766, 2007.
Thominiaux, C., Done, F., James, M. L., Bramoulle, Y., Boutin, H., Besret, L., et al. (2006). Improved synthesis of the peripheral benzodiazepine receptor ligand [ 11C]DPA-713 using [11C]methyl triflate. Applied Radiation and Isotopes, 64(5), 570-573.
Tifft et al., Annals of Medicine, vol. 29, No. 6, pp. 557-561, 1997.
Veenman et al., Drug Dev. Res., vol. 50, No. 3-4, pp. 355-370, 2000.

(Continued)

*Primary Examiner* — Michael G Hartley
*Assistant Examiner* — Jagadishwar Samala
(74) *Attorney, Agent, or Firm* — Ward and Smith, P.A.

(57) ABSTRACT

Translocator protein (TSPO) targeting compounds are described. Methods of making the compounds, and uses of the compounds for imaging are also described.

17 Claims, 24 Drawing Sheets

(56) References Cited

OTHER PUBLICATIONS

Veiga et al. Glia, vol. 55, No. 14, pp. 1426-1436, 2007.
Venneti et al., J. Clin. Invest., vol. 113, No. 7, pp. 981-989, 2004.
Versijpt et al., Eur. Neurol., vol. 50, No. 1, pp. 39-47, 2003.
Visigalli et al., Neurobiol. Dis., vol. 34, No. 1, pp. 51-62, 2009.
Vowinckel et al., J. Neurosci. Res., vol. 50, No. 2, pp. 345-353, 1997.
Wada et al, Proc. Natl. Acad. Sci. USA, vol. 97, No. 20, pp. 10954-10959, 2000.
Wang et al., Biochem. Biophy. Res. Comm., vol. 389, No. 1, pp. 80-83, 2009.
Wunder et al., Neuroscience, vol. 158, pp. 1161-1173, 2009.
Yamanaka et al., Genomics, vol. 21, No. 3, pp. 588-596, 1994.

* cited by examiner

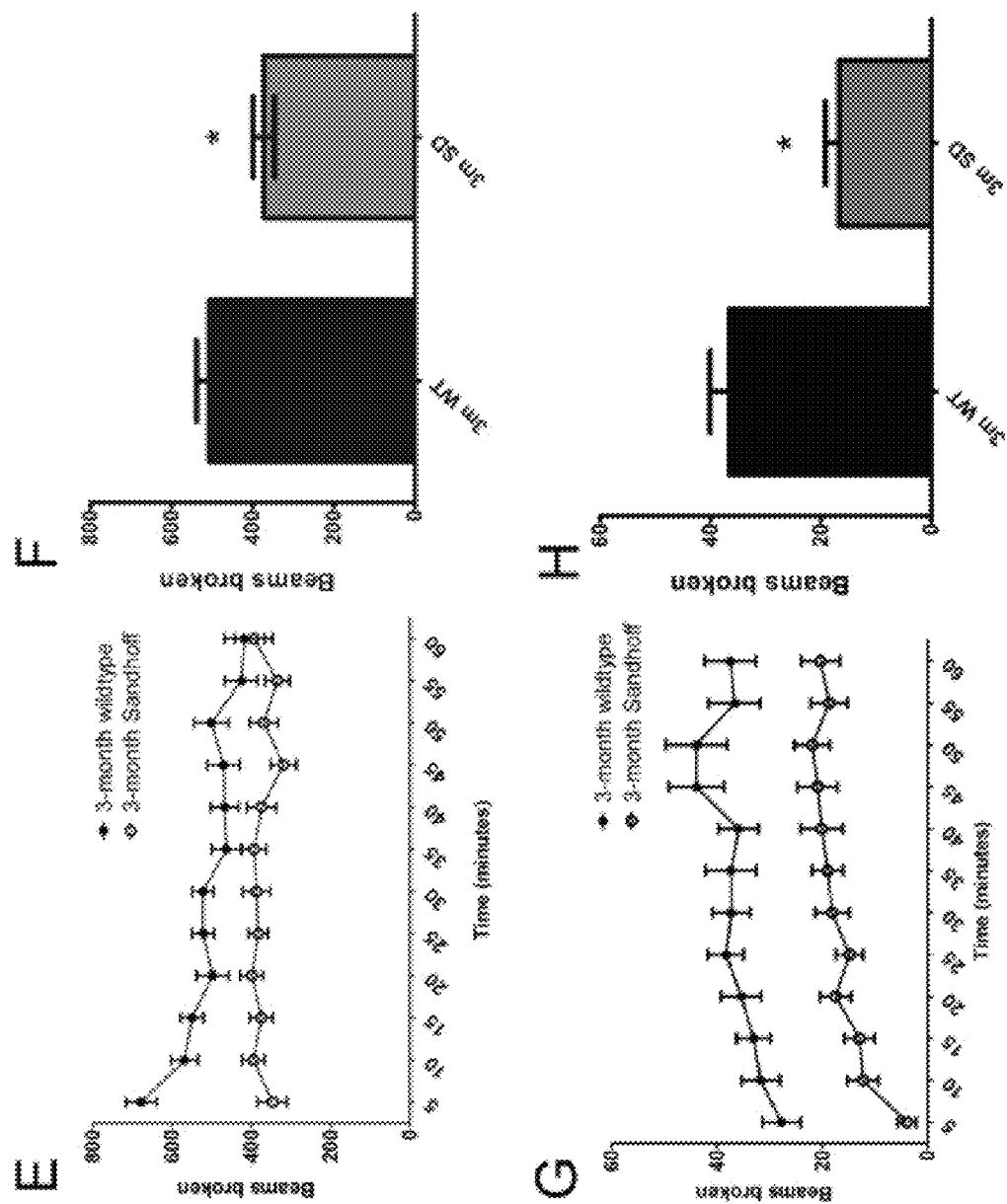
Figure 5, cont.

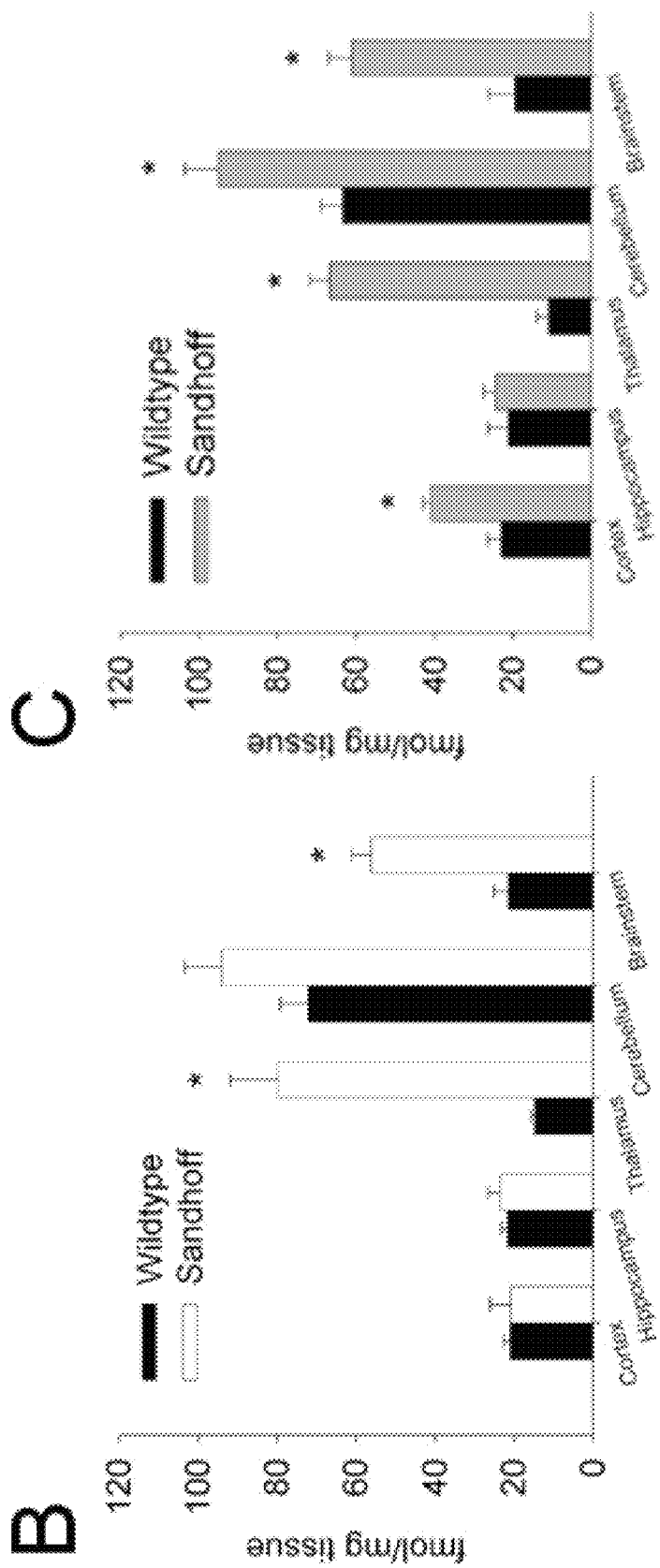
Figure 7, cont.

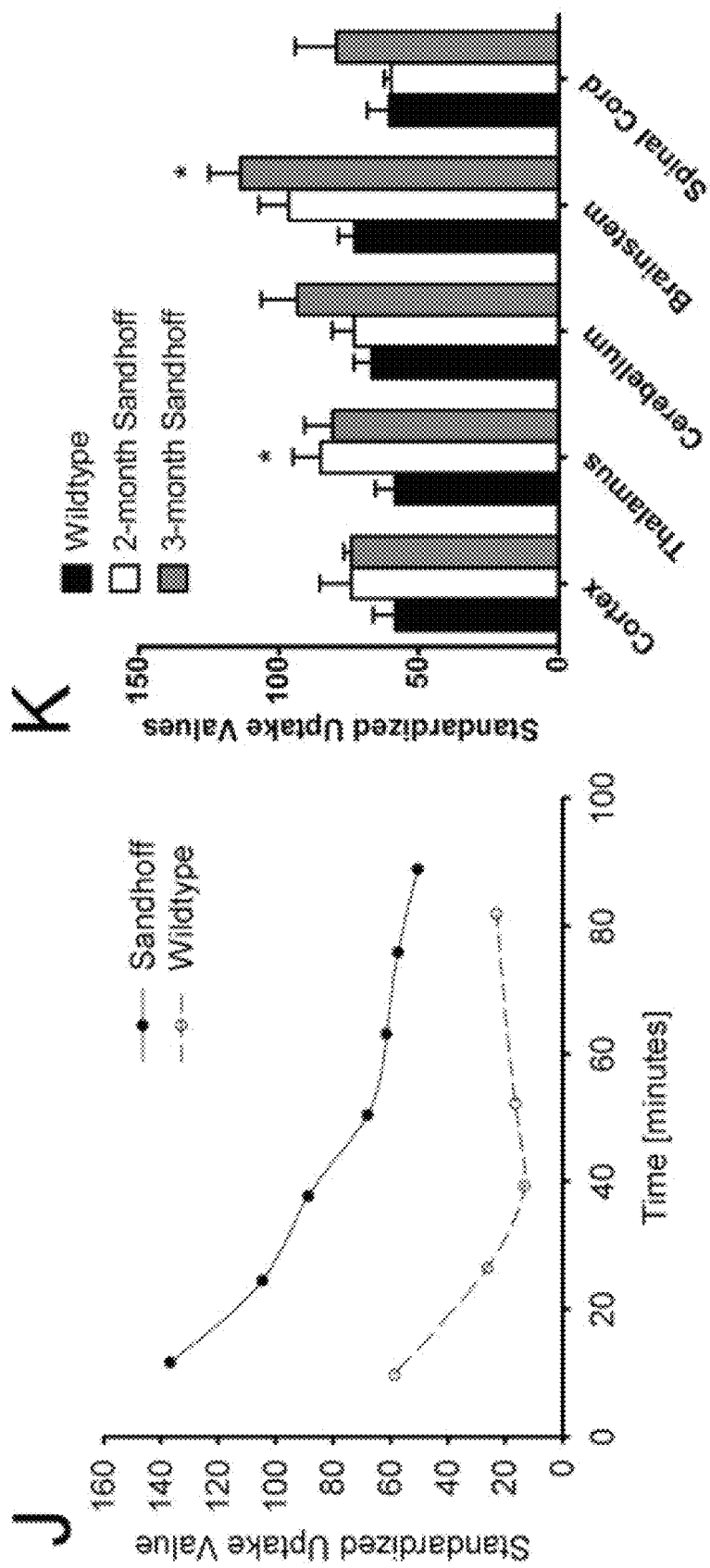
Figure 8, cont.

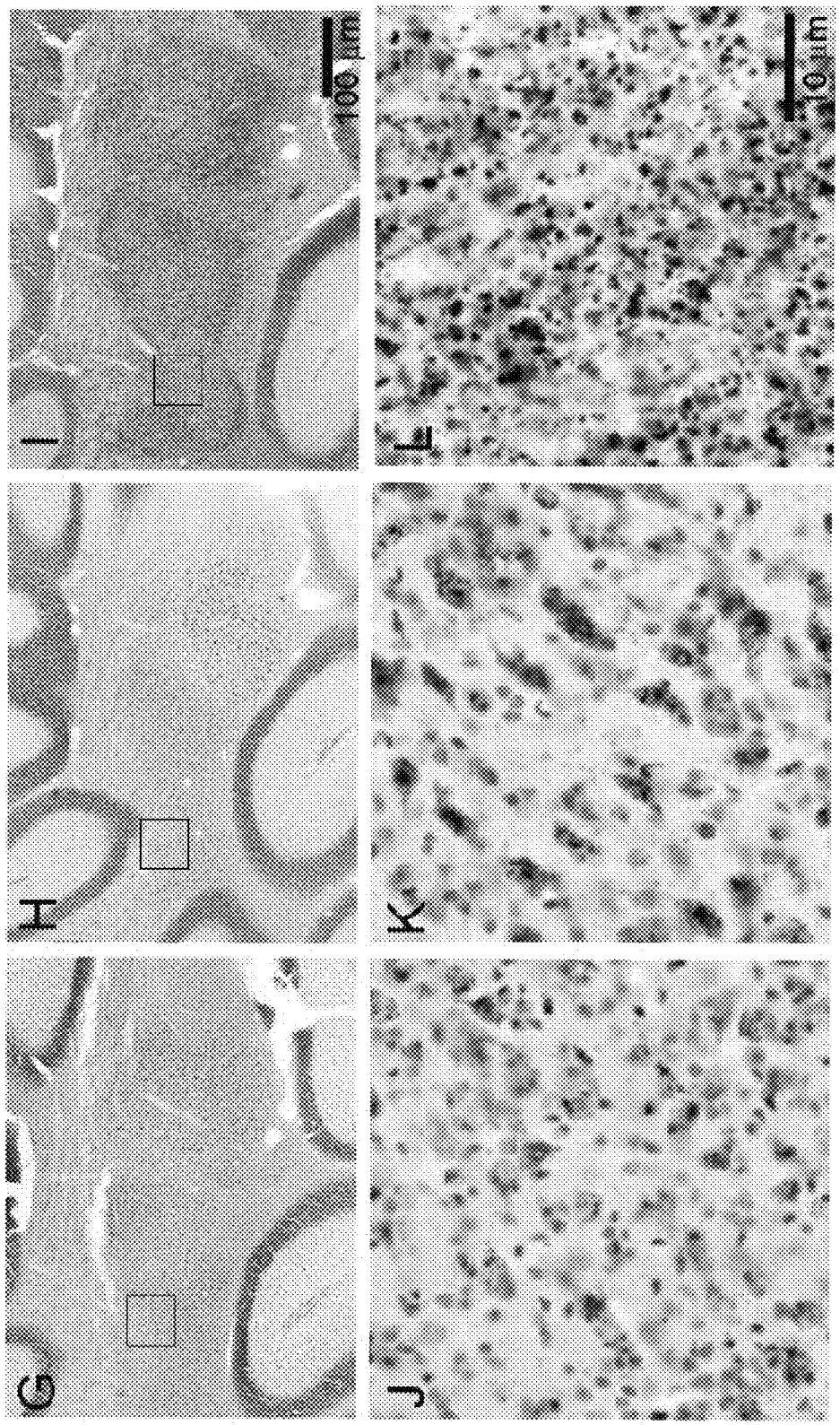
Figure 9, cont.

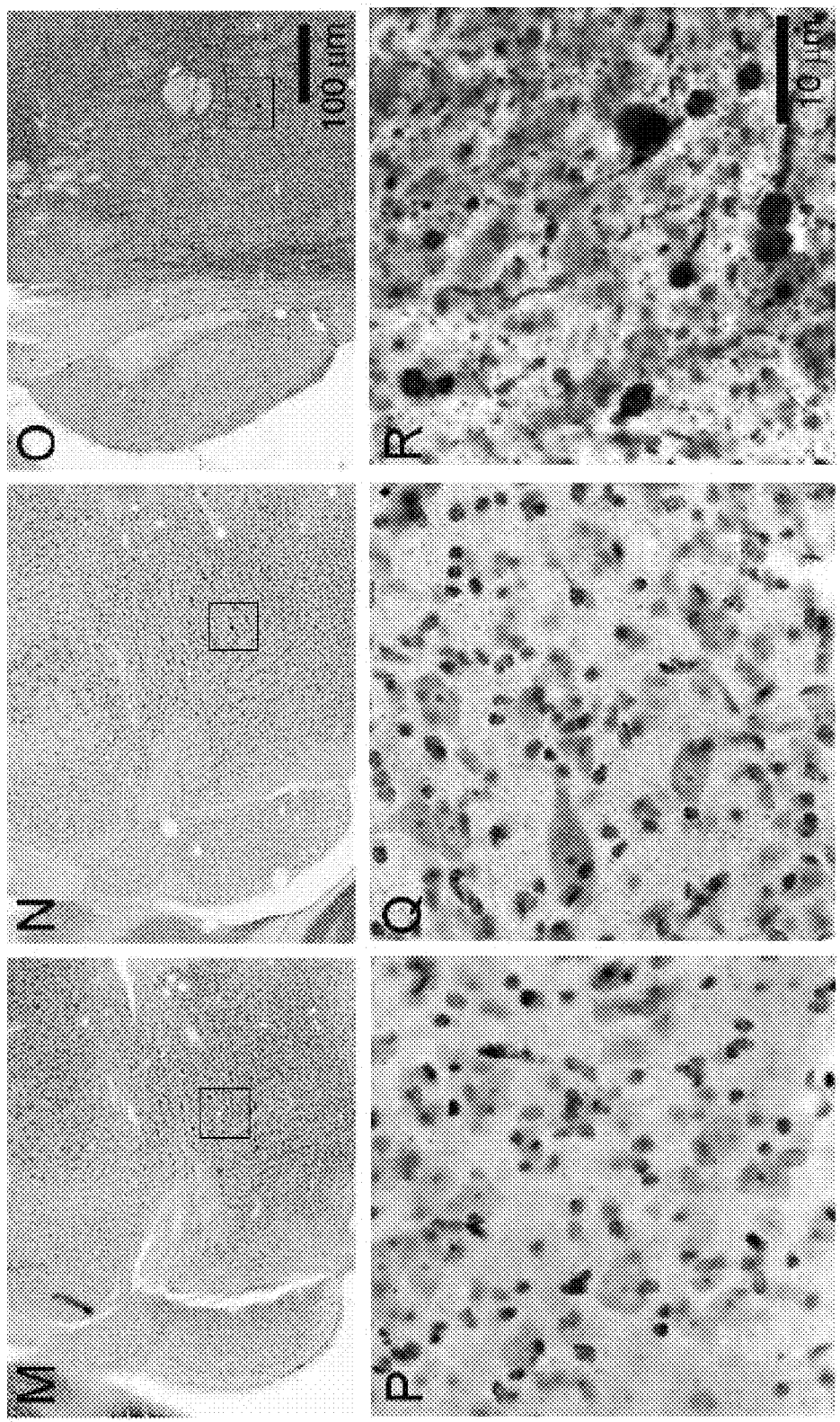
Figure 9, cont.

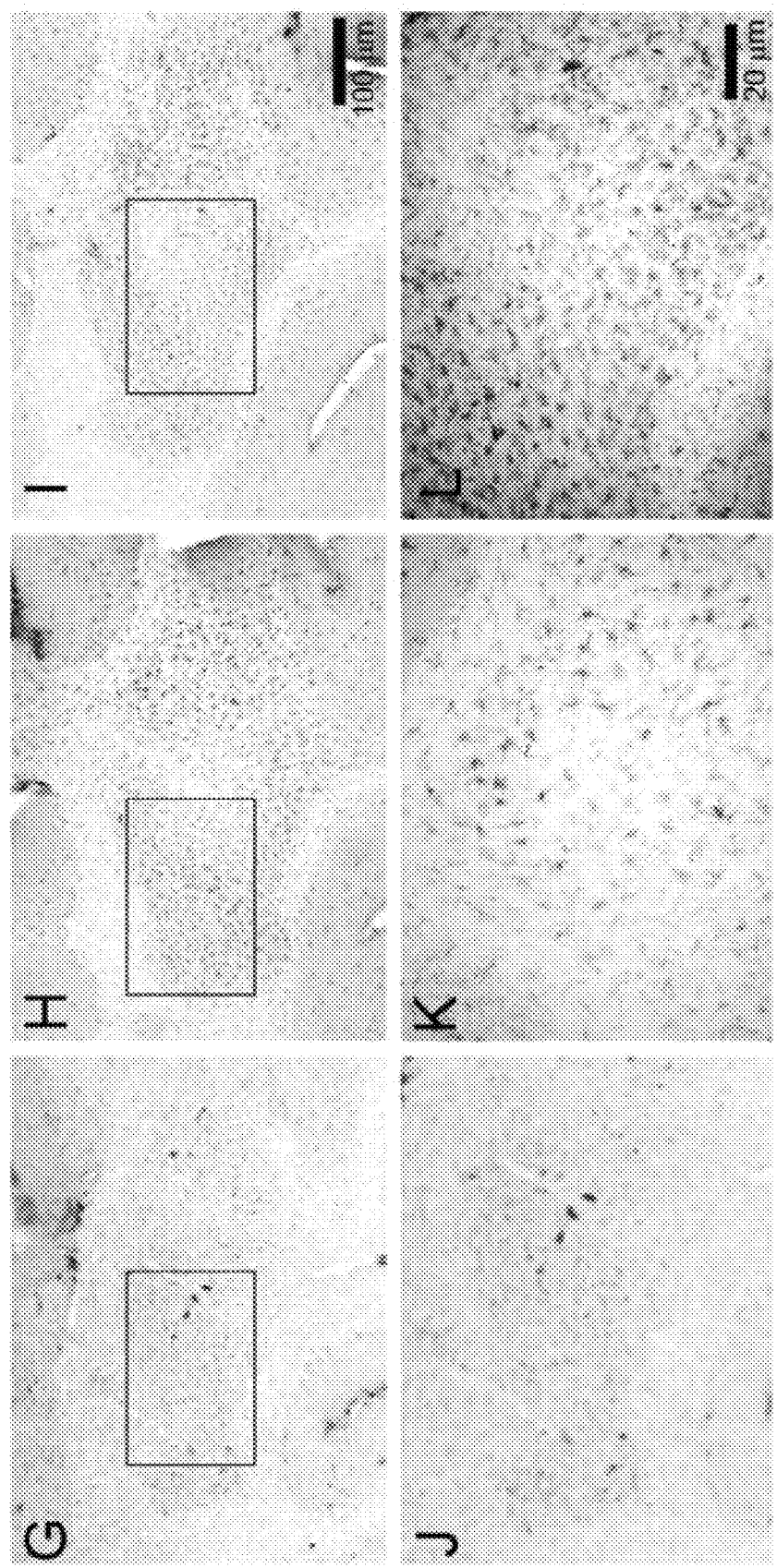
Figure 10, cont.

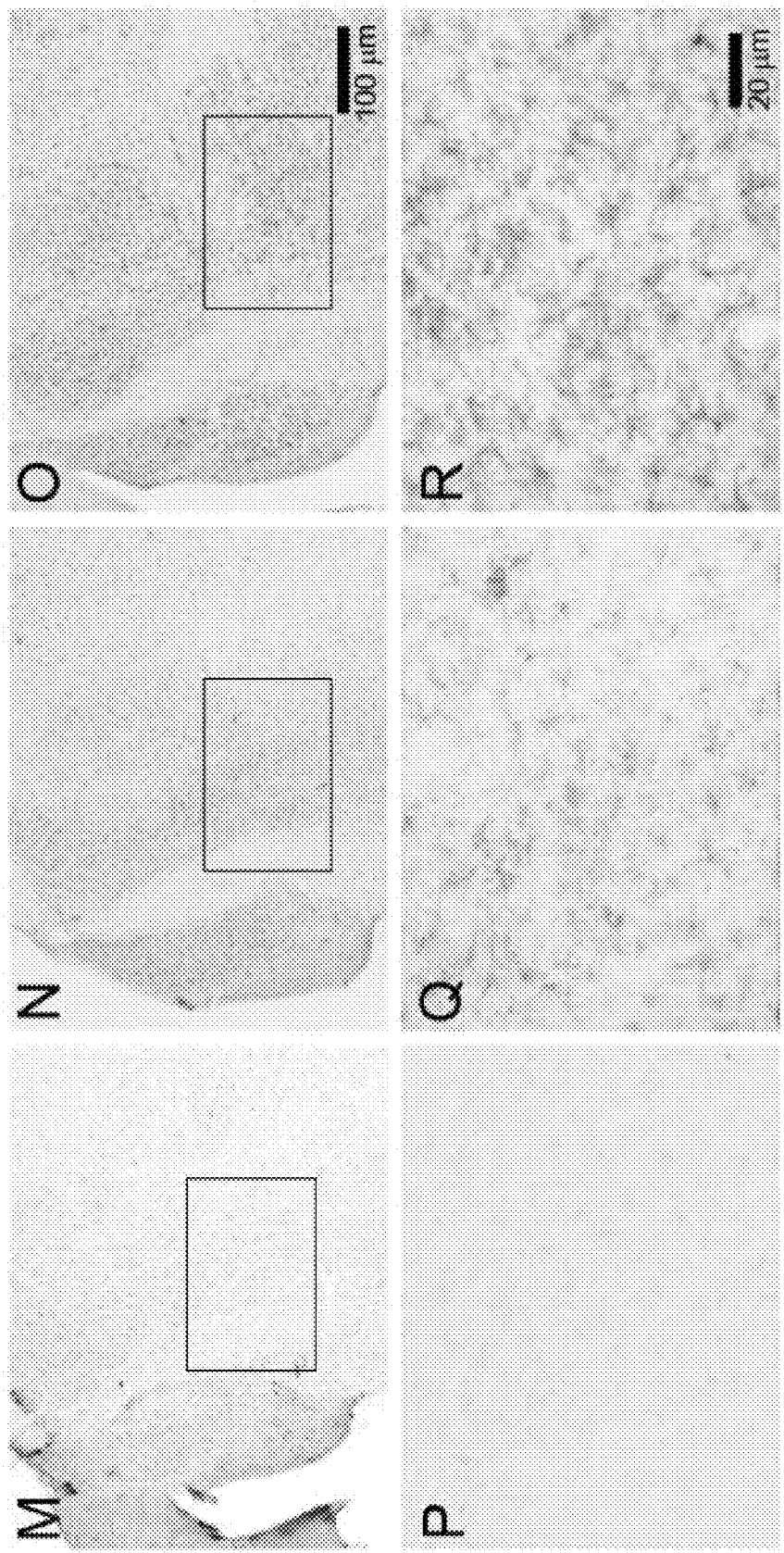
Figure 10, cont.

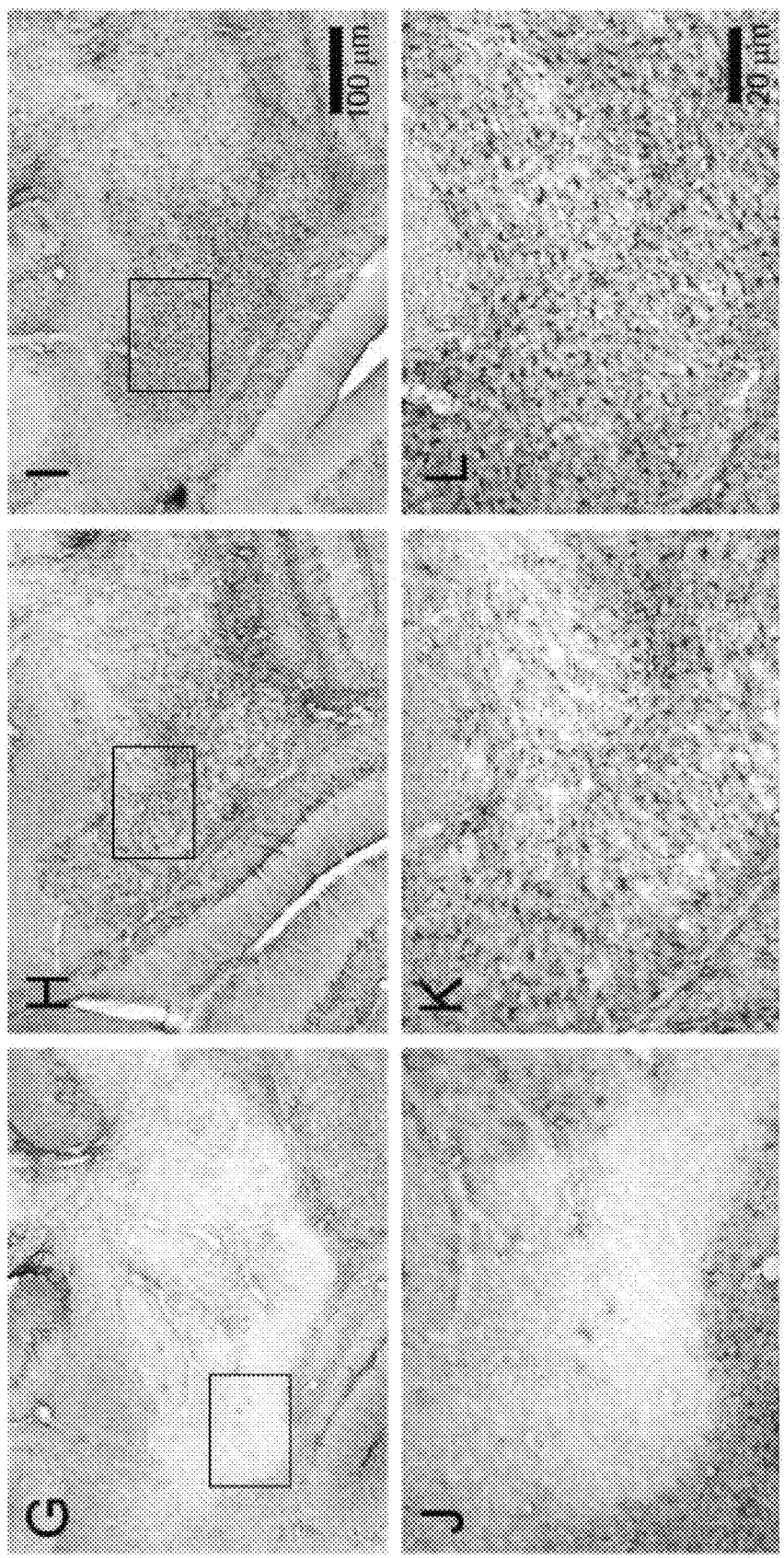
Figure 11, cont.

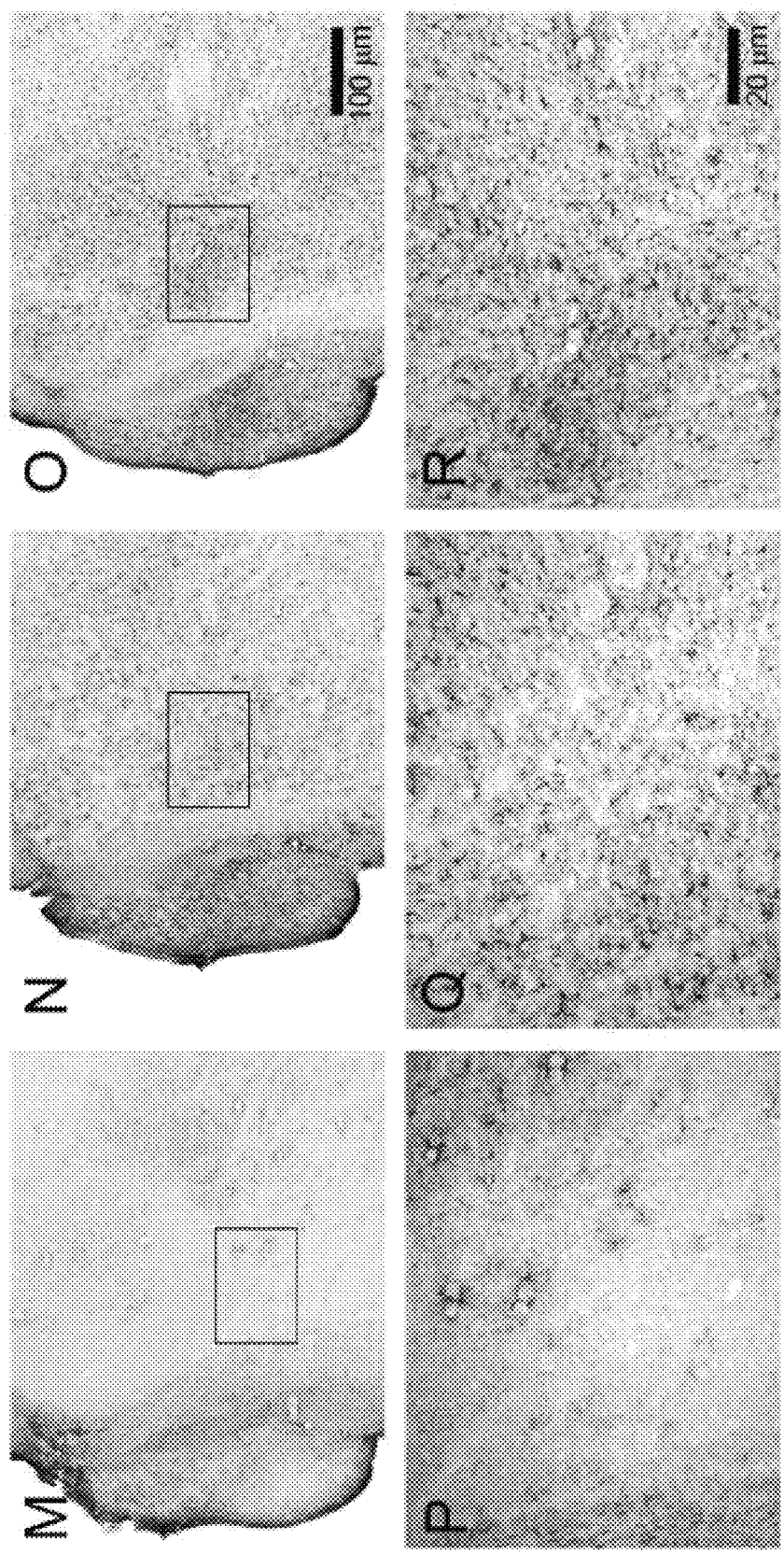
Figure 11, cont.

TSPO-TARGETING COMPOUNDS AND USES THEREOF

CROSS-REFERENCE TO RELATED APPLICATION

This application claims priority to U.S. Provisional Application No. 61/307,557 filed Feb. 24, 2010. The entire content of the Provisional Application is hereby incorporated by reference in its entirety.

This invention was made using U.S. Government support under NIH grant CA092871. The government has certain rights in this invention.

BACKGROUND

Field of the Invention

Translocator protein, (TSPO, (18 kDa)), formerly known as the peripheral benzodiazepine receptor (PBR), has been widely used as a sensitive biomarker of brain injury and inflammation. It is known that TSPO expression increases dramatically in glial cells, particularly in microglia and astrocytes, as a result of brain injury, and this phenomenon is a component of reactive gliosis.

Inflammation is becoming an increasingly important target for imaging, particularly in the context of central nervous system disease (Wunder et al., Neuroscience, vol. 158, pp. 1161-1173, 2009; Cagnin et al., Neurotherapeutics, vol. 4, pp. 443-452, 2007). Imaging agents are also being sought to study autoimmune disease and the inflammatory arthritides, the cardiovascular system and cancer. For nearly 20 years the standard radiopharmaceutical for imaging inflammation has been the isoquinoline [$^{11}$C]PK11195, a ligand for TSPO, which is upregulated in activated glial and immune cells (Chen et al., Pharmacol. Ther., vol. 118, pp. 1-17, 2008; Scarf et al., J. Med. Chem., vol. 52, pp. 581-592, 2009). But [$^{11}$C]PK11195 tends to demonstrate significant non-specific binding and poor brain uptake (Endres et al., J. Nucl. Med., vol. 50, pp. 1276-1282, 2009; Chauveau et al., J. Nucl. Med., vol. 50, pp. 468-476, 2009), so superior radioligands for TSPO have been aggressively sought (Cagnin et al., Neurotherapeutics, vol. 4, pp. 443-452, 2007). One such class of compounds that could be derivatized for imaging TSPO includes the pyrazolopyrimidines, in particular N,N-diethyl-2-[2-(4-methoxy-phenyl)-5,7-dimethyl-pyrazolo[1,5-a]pyrimidin-3-yl]-acetamide, DPA-713 (James et al., Bioorg. Med. Chem., vol. 13, pp. 6188-6194, 2005; Boutin et al., J. Nucl. Med., vol. 48, pp. 573-581, 2007). DPA-713 is 10-fold less lipophilic than PK11195 and has nearly twice the affinity for TSPO. James et al. synthesized [$^{11}$C]DPA-713, which demonstrated higher signal-to-noise ratios than [$^{11}$C]PK11195 in a rodent model of brain injury (Doorduin et al., Mol. Imag. Biol., vol. 11, no. 6, pp. 386-398, 2009; Boutin et al., J. Nucl. Med., vol. 48, pp. 573-581, 2007). The first human study of [$^{11}$C]DPA-713 was recently undertaken, which demonstrated a higher binding potential than [$^{11}$C]PK11195 (Endres et al., J. Nucl. Med., vol. 50, pp. 1276-1282, 2009). However, $^{11}$C-labeled radiopharmaceuticals are limited to centers in which there is a cyclotron on site, can be difficult to handle due to the 20 min physical half-life of the radionuclide, and the synthesis of such compounds can be prohibitively costly for preclinical (small animal) imaging studies.

Reactive gliosis, characterized by the activation of microglia and astrocytes, is the hallmark response of the central nervous system (CNS) when there is injury or inflammation. During reactive gliosis, TSPO is highly expressed in glial cells at specific regions that have been injured (Chen et al., Pharmacol. Ther. Vol. 118, no. 1, pp. 1-17, 2008; Papadopoulos et al., Exp. Neurol., vol. 219, no. 1, pp. 53-57, 2009; Veenman et al., Drug Dev. Res., vol. 50, no. 3-4, pp. 355-370, 2000). While most studies have associated increased TSPO levels with activated microglia (Vowinckel et al., J. Neurosci. Res., vol. 50, no. 2, pp. 345-353, 1997; Banati et al., Brain, vol. 123, no. 11, pp. 2321-2337, 2000; Venneti et al., J. Clin. Invest., vol. 113, no. 7, pp. 981-989, 2004), previous works have found that TSPO is also expressed in reactive astrocytes (Kuhlmann et al., J. Neurochem., vol. 74, no. 4, pp. 1694-1704, 2000; Chen et al., Brain, vol. 127, no. 6, pp. 1379-1392, 2004; Maeda et al., Brain Res. vol. 1157, pp. 100-111, 2007; Cosenza-Nashat et al., Neuropathol. Applied Neurobiol., vol. 35, no. 3, pp. 306-328, 2009). Using [$^3$H]-(R)-PK11195 emulsion microautoradiography or TSPO immunohistochemistry to detect TSPO levels on brain sections stained with Mac-1 (a microglia specific marker) or GFAP (an astrocyte specific marker), studies have shown that increased [$^3$H]-(R)-PK11195 binding to TSPO can be observed in both microglia and astrocytes in a chemically-induced model of brain injury (Kuhlmann et al., J. Neurochem., vol. 74, no. 4, pp. 1694-1704, 2000). Another study using local injection of ethanol into rat straitum showed colocalization of TSPO with microglia or astrocytes in a time-dependent manner. TSPO colocalization with microglia persisted 30 days after ethanol injection, but astrocytes showed colocalization with TSPO only 7 days after ethanol injection. TSPO in astrocytes was not seen 30 days after injection even though GFAP-positive astrocytes were still highly detectable (Maeda et al., Brain Res., vol. 1157, pp. 100-111, 2007). Increased TSPO expression has been demonstrated to be colocalized in microglia and astrocytes in a chemically-induced mouse model of demyelination. In this model, it appeared that there is a temporal shift in the TSPO increase from microglia to astrocytes. Furthermore, TSPO levels decrease as the gliosis resolves (Chen et al., Brain, vol. 127, no. 6, pp. 1379-1392, 2004). In humans, TSPO colocalization with both microglia and astrocytes has been shown to be present in brain tissues of HIV encephalitis patients (Cosenza-Nashat et al., Neuropathol. Applied Neurobiol., vol. 35, no. 3, pp. 306-328, 2009).

Because TSPO is able to track both increased gliosis and the resolution of gliosis when injured tissue recovers, it serves as a sensitive marker to neurodegenerative changes and inflammation. The use of TSPO as a biomarker of brain injury has been demonstrated with chemical-induced neurotoxicity (Guilarte et al., Neurotoxicology, vol. 16, no. 3, pp. 441-450, 1995; Kuhlmann et al., Brain Research, vol. 751, no. 2, pp. 281-288, 1997; Kuhlmann et al., Toxicol. Sci., vol. 48, no. 1, pp. 107-116, 1999; Kuhlmann et al., J. Neurochem., vol. 74, no. 4, pp. 1694-1704, 2000; Guilarte et al., Neuroscience, vol. 122, no. 2, pp. 499-513, 2003; Chen et al., Brain, vol. 127, no. 6, pp. 1379-1392, 2004; Chen et al., Toxicol. Sci., vol. 91, no 2, pp. 532-539, 2006), ischemic stroke (Gerhard et al., Neuroreport., vol. 11 no. 13, pp. 2957-2960, 2000; Gerhard et al., NeuroImage, vol. 24, no. 2, pp. 591-595, 2005; Pappata et al. Neurology, vol. 55, no. 7, pp. 1052-1054, 2000; Price et al., Stroke, vol. 37, no. 7, pp. 1749-1750, 2006), physical trauma (Miyazawa et al., Acta Neurochir., vol. 137, no. 3-4, pp. 207-16, 1995; Raghavendra et al., Exp. Neurol., vol. 161, no. 1, pp. 102-114, 2000), and neurodegenerative diseases such as Alzheimer's disease (Cagnin et al., Lancet, vol. 358, no. 9280, pp. 461-467, 2001; Versijpt et al., Eur. Neurol., vol. 50, no. 1, pp. 39-47, 2003; Ouchi et al., Ann. Neurol., vol. 57, no. 2, pp. 168-175, 2005; Gerhard et al., Neurobiol. Dis., vol. 21, no. 2, pp. 404-412, 2006; Tai et al., Brain, vol. 130, no. 7, pp. 1759-1766, 2007). While TSPO has been extensively used for in vivo imaging both in rodents and in humans, most of the studies have been cross-sectional in nature.

Sandhoff disease is an autosomal recessive neurodegenerative disease characterized by excess glycolipid storage due to the lack of lysosomal β-hexosaminidase, resulting in impaired degradation of $G_{M2}$ and $G_{A2}$ gangliosides and other glycolipids (Jeyakumar et al., Neuropathol. Applied Neurobiol., vol. 28, no. 5, pp. 343-357, 2002). Because gangliosides are expressed in high amount in the central nervous system (CNS), the brain is one of the most affected organs (Jeyakumar et al., Neuropathol. Applied Neurobiol., vol. 28, no. 5, pp. 343-357, 2002). In humans, the onset of the infantile form of Sandhoff disease occurs around 6 months of age with symptoms such as motor weakness, early blindness, macroencephaly (enlarged head), and seizures. Symptoms progress rapidly, and death occurs between ages 3 to 5 due to mainly respiratory infections (Jeyakumar et al., Neuropathol. Applied Neurobiol., vol. 28, no. 5, pp. 343-357, 2002; Maegawa et al., Pediatrics, vol. 118, no. 5, pp. e1550-1562, 2006).

β-hexosaminidase is formed by the dimerization of two subunits, α- and β-subunits to form β-hexosaminidase A (αβ) or two β subunits to form β-hexosaminidase B (ββ). In the mouse model of Sandhoff disease, the gene encoding for the β subunit of β-hexosaminidase (HexB) is disrupted, resulting in the deficiency of β-hexosaminidase A and B (Yamanaka et al., Genomics, vol. 21, no. 3, pp. 588-596, 1994). This deficiency results in impaired degradation and accumulation of $G_{M2}$ and $G_{A2}$ gangliosides in neurons (Sango et al., Nature Genetics, vol. 11, no. 2, pp. 170-176, 1995), resulting in severe neurodegeneration in the brain (Wada et al., Proc. Natl. Acad. Sci. USA, vol. 97, no. 20, 10954-10959, 2000). Sandhoff (HexB KO) mice exhibit spastic and reduced hind limb movements with progressive motor deficit around 3 months of age (Sango et al., Nature Genetics, vol. 11, no. 2, pp. 170-176, 1995). The life span of Sandhoff mice is approximately 5 months after birth as the mice have lost ability to move and are unable to retrieve food or water (Sango et al., Nature Genetics, vol. 11, no. 2, pp. 170-176, 1995; Tifft et al., Annals of Medicine, vol. 29, no. 6, pp. 557-561, 1997; Jeyakumar et al., Neuropathol. Applied Neurobiol., vol. 28, no. 5, pp. 343-357, 2002). Histopathological studies have shown that excess storage of glycolipid leads to neuronal apoptosis in the cerebral cortex, cerebellum, brainstem, spinal cord, trigeminal ganglion, retina, thalamus in the Sandhoff mice, and neuronal apoptosis has been seen in those regions (Sango et al., Nature Genetics, vol. 11, no. 2, pp. 170-176, 1995; Wada et al., Proc. Natl. Acad. Sci. USA, vol. 97, no. 20, pp. 10954-10959, 2000). Tissues from humans diagnosed with Sandhoff disease have also shown neurodegeneration in spinal cord, thalamus, and cortex (Huang et al., Hum. Mol. Genet., vol. 6, no. 11, pp. 1879-1885, 1997; Wada et al., Proc. Natl. Acad. Sci. USA, vol. 97, no. 20, pp. 10954-10959, 2000). Thus, the mouse model of Sandhoff disease shares many of the clinical symptoms and neuropathology as the human version of the disease.

Previous work has shown that microglia become activated in both the mouse model and in human cases of Sandhoff disease (Wada et al., Proc. Natl. Acad. Sci. USA, vol. 97, no. 20, pp. 10954-10959, 2000; Visigalli et al., Neurobiol. Dis., vol. 34, no. 1, pp. 51-62, 2009). Further, it appears that microglia activation precedes neuronal degeneration. cDNA microarray analysis has also shown increased TSPO gene expression in the Sandhoff disease mice (Wada et al, Proc. Natl. Acad. Sci. USA, vol. 97, no. 20, pp. 10954-10959, 2000), and using PET imaging, uptake of [$^{11}$C]-PK11195, a TSPO-specific ligand, was higher in Sandhoff mice at 4 months of age compared to wildtype (Visigalli et al., Neurobiol. Dis., vol. 34, no. 1, pp. 51-62, 2009). However, a longitudinal assessment of TSPO in Sandhoff disease and its comparison with behavioral endpoints has not been thoroughly investigated. Furthermore, it has been previously reported that [$^{11}$C]-PK11195 show significant non-specific binding and poor brain uptake (Boutin et al., J. Nucl. Med., vol. 48, no. 4, pp. 573-581, 2007; Endres et al., J. Nucl. Med., vol. 50, no. 8, pp. 1276-1282, 2009).

SUMMARY OF THE INVENTION

The present invention satisfies the long standing and unmet need for new imaging compounds for imaging inflammation.

Embodiments of the invention include compounds having the structure

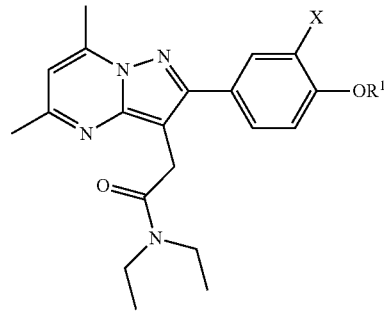

where X is H, I, $^{123}$I, $^{124}$I, $^{125}$I, or $^{131}$I, and $R^1$ is H or $CH_3$, with the proviso that when X is H, $R^1$ is not $CH_3$. Embodiments of the invention include compounds having the structure

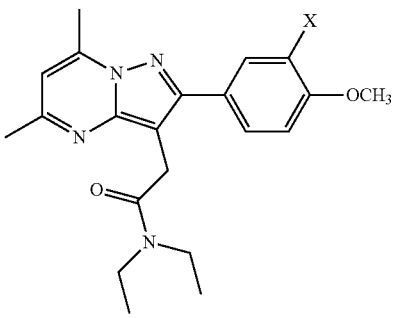

where X is I, $^{123}$I, $^{124}$I, $^{125}$I, or $^{131}$I. Further embodiments of the invention include any of the above compounds isotopically enriched in one of $^{123}$I, $^{124}$I, $^{125}$I, or $^{131}$I.

Other embodiments include methods for preparing compounds having the structure

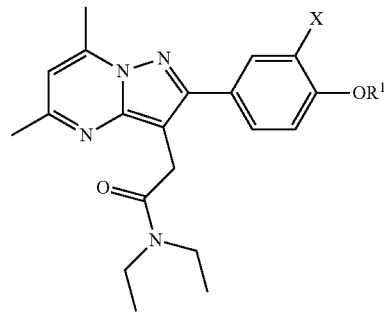

where X is I, $^{123}$I, $^{124}$I, $^{125}$I, or $^{131}$I; and R$^1$ is H or CH$_3$, by reacting

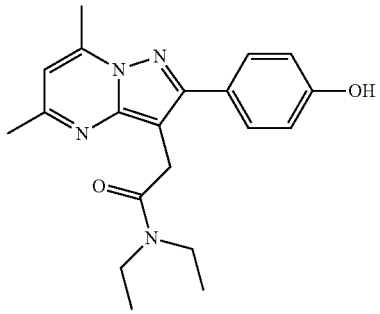 [SMILES: CCN(CC)C(=O)Cc1c(-c2ccc(O)cc2)nn2c(C)cc(C)nc12]

with iodide in the presence of iodogen or chloramine-T, where the iodide may be isotopically enriched in one of $^{123}$I, $^{124}$I, $^{125}$I, or $^{131}$I. The method may further include reacting

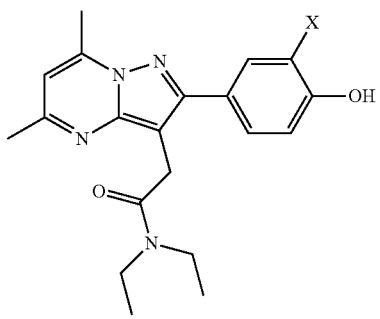

where X is I, $^{123}$I, $^{124}$I, $^{125}$I, or $^{131}$I with a methylating agent.

Other embodiments include methods for imaging cells, tissues, a sample, an organ or a subject by imaging cells, a sample, an organ or a subject with elevated levels of translocator protein, TSPO, after administration of a detectably sufficient amount of a radioisotopically-enriched compound having the structure

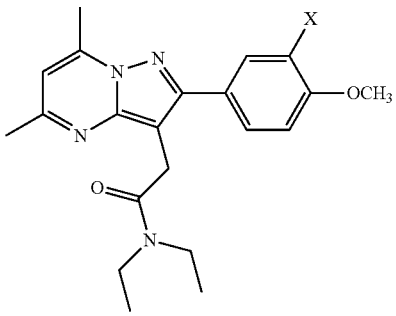

where X is $^{123}$I, $^{124}$I, $^{125}$I, or $^{131}$I. The method may further include administering, before imaging, a detectably sufficient amount of a radioisotopically-enriched compound having the structure

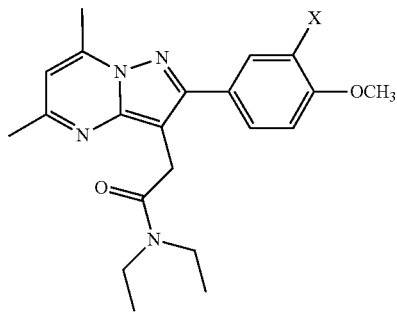

where X is $^{123}$I, $^{124}$I, $^{125}$I, or $^{131}$I.

Embodiments include methods where imaging is performed by autoradiography, single photon emission computed tomography, or positron emission tomography. In some embodiments, the imaging is autoradiography. In some embodiments, imaging is single photon emission computed tomography and the compound is radioisotopically-enriched with $^{123}$I or $^{125}$I. In some embodiments, the imaging is positron emission tomography and the compound is radioisotopically-enriched with $^{124}$I.

In some embodiments, the cells being imaged are glial cells or immune cells.

In some embodiments, the organ being imaged is the brain. In some embodiments, the organ being imaged is the lungs. In some embodiments, the organ being imaged is the heart.

In some embodiments, the subject being imaged has inflammation. In some embodiments, the subject being imaged has an autoimmune disease. In some embodiments, the subject being imaged has inflammatory arthritides. In some embodiments, the subject being imaged has a neurodegenerative disease. In some embodiments, the subject being imaged has atherosclerosis. In some embodiments, the subject being imaged has myocarditis. In some embodiments the subject being imaged has pneumonitis. In some embodiments the subject being imaged has pneumonia.

BRIEF DESCRIPTION OF THE DRAWINGS

FIG. 5B shows the average values of total locomotor activity (FIG. 5B) and rearing (FIG. 5D) between wildtype and 2-month Sandhoff mice over 1 hour (n=11-13 male mice per group). (FIG. 5E) At 3 months, Sandhoff mice exhibited dramatic decrease in locomotor activity (FIG. 5E) and rearing (FIG. 5G) over 1 hour. The average values of locomotor activity (FIG. 5F) and rearing (FIG. 5H) over 1 hour between wildtype and 3-month Sandhoff mice showed the significant decrease. Data is expressed as mean±SEM (n=13-14 male mice per group, p<0.05 compared to wildtype).

FIG. 7A shows representative autoradiograms of [$^{125}$I]-IodoDPA713 binding to TSPO in horizontal mouse brain sections for wildtype, 2-month Sandhoff, and 3-month Sandhoff mice. TSPO binding increased in thalamus and brainstem of both 2- and 3-month Sandhoff mice. 1=thalamus; 2=brainstem; 3=hippocampus; 4=cortex; 5=cerebellum. FIG. 7B shows specific binding of [$^{125}$I]-IodoDPA713 in various brain regions between wildtype (n=5) and Sandhoff (n=5) at 2 months. FIG. 7C shows specific binding of [$^{125}$I]-IodoDPA713 in various brain regions between wildtype (n=5) and Sandhoff (n=5) at 3 months. At this time point, increased TSPO binding was observed in the cortex as well as cerebellum. Each value represents the mean±SEM (*p<0.05 compared to wildtype).

FIG. 8(J) shows time-activity curve showing the uptake of [$^{125}$I]IodoDPA-713 in the thalamus of wildtype and of Sandhoff mice. Three-month Sandhoff mouse had consistently higher uptake of [$^{125}$I]-IodoDPA713 than wildtype. FIG. 5K shows quantitative analysis of tracer uptake showed that Sandhoff mice showed a trend of higher [$^{125}$I]-IodoDPA713 uptake compared to wildtype. For 2-month Sandhoff mice, there was a significant increase in [$^{125}$I]-IodoDPA713 uptake in the thalamus. For 3-month Sandhoff mice, there was a significant increase in [$^{125}$I]-IodoDPA713 uptake in the brainstem. Images are expressed in units of SUV and thus are normalized for weight and injected dose. Data is expressed as the mean of Standardized Unit Value±SEM (n=3-4 male mice per group, *p<0.05 compared to wildtype)

Figure 12:
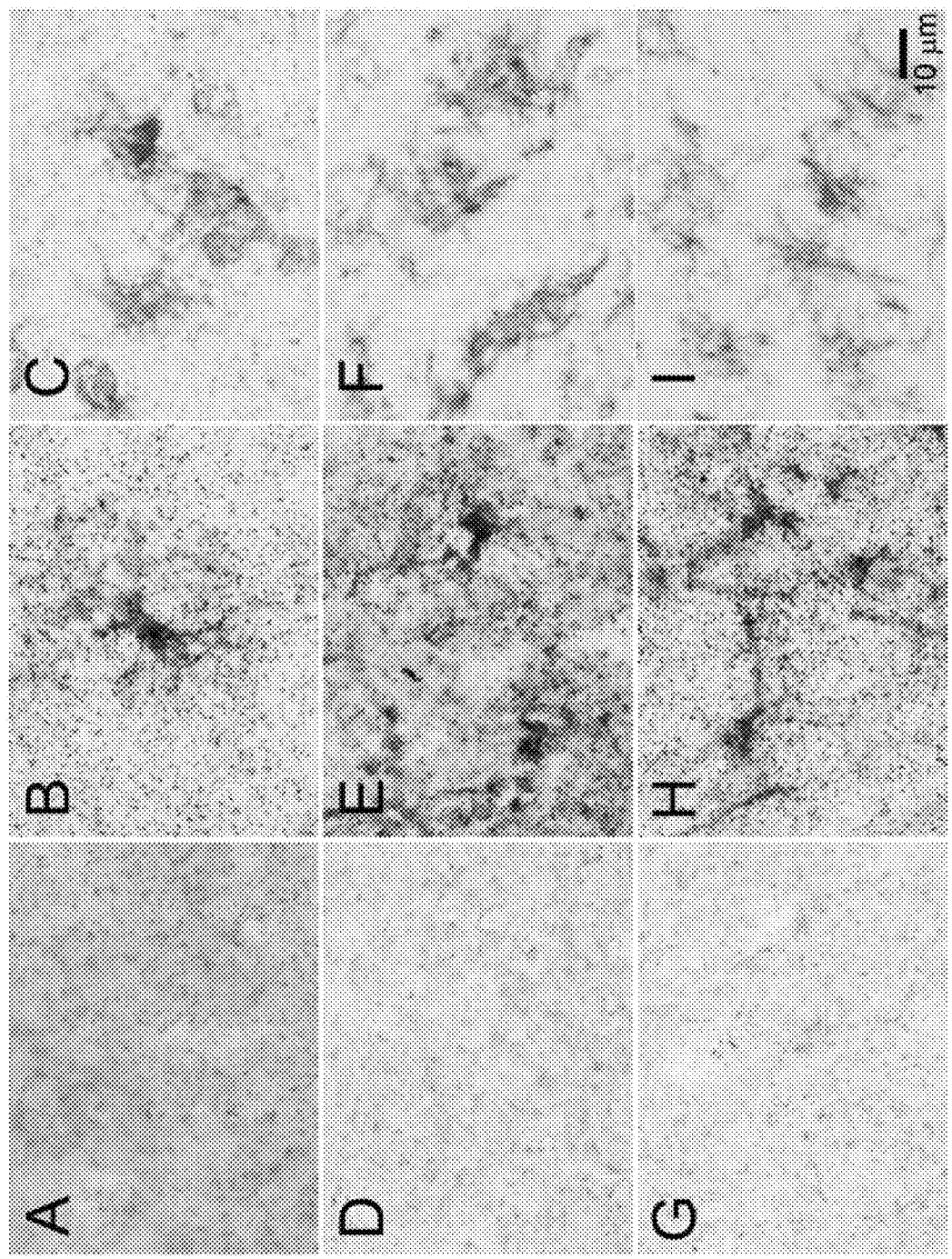
FIG. 12 shows TSPO binding is co-localized in activated microglia in regions affected by Sandhoff disease. Representative micrographs showing TSPO binding via high-resolution [$^3$H]-(R)-PK11195 emulsion autoradiography as indicated by silver grain density in conjunction with Mac-1 immunohistochemistry to determine the cellular localization of TSPO binding. Wildtype mice showed little to no silver grain nor detection of activated microglia in thalamus (FIG. 12A), cerebellum (FIG. 12D), and brainstem (FIG. 12G).

Sandhoff mice showed increased silver grain density, indicative of increased TSPO binding, co-localized in activated microglia in the thalamus (FIG. 12B), cerebellum (FIG. 12E), and brainstem (FIG. 12H). The increased binding in Sandhoff mice appeared to be specific as high concentration of nonradiolabeled PK11195 competed with [$^3$H]-(R)-PK11195 binding (FIG. 12C for thalamus, FIG. 12F for cerebellum, and FIG. 12I for brainstem). Scale bar=10 μm.

Figure 13:
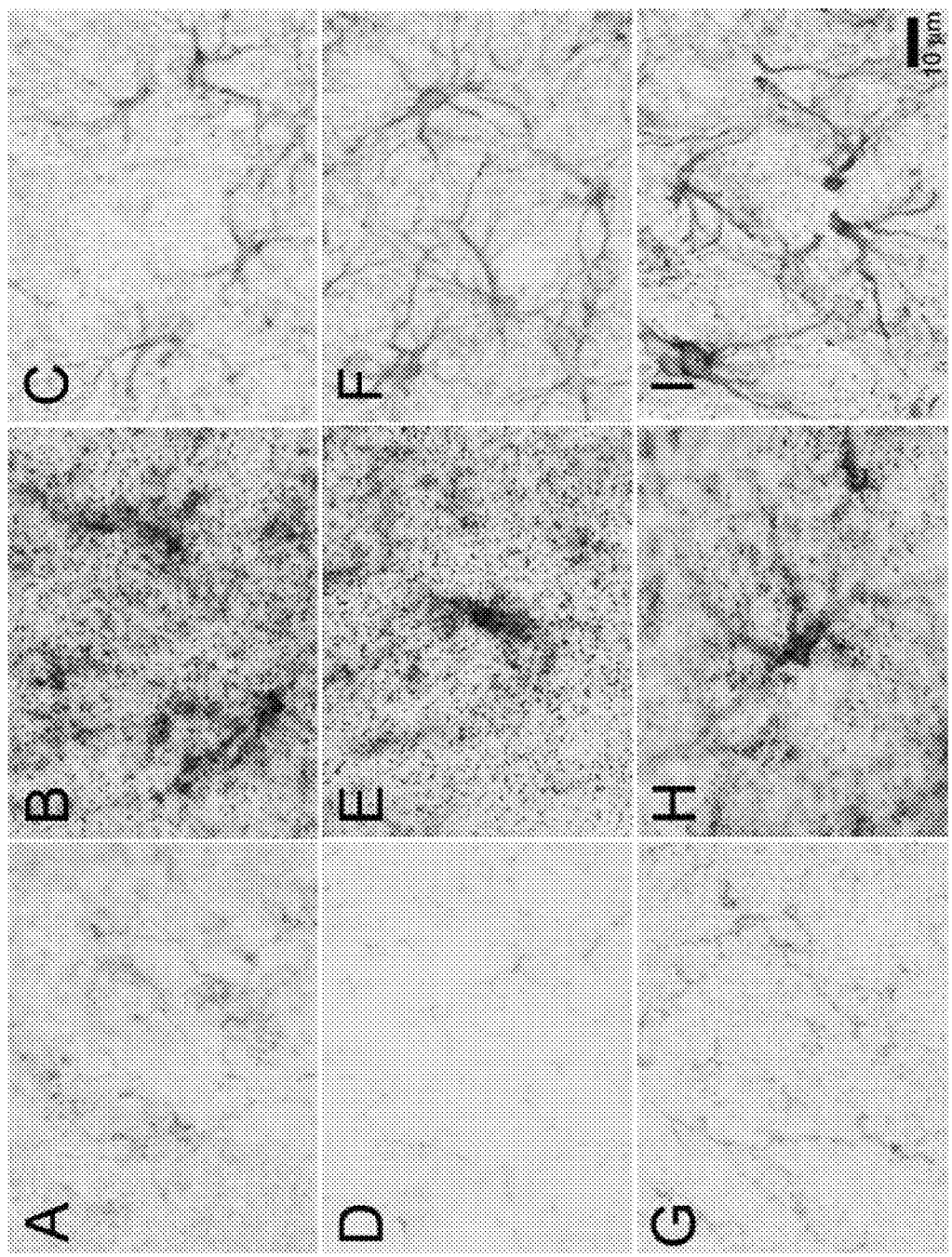

FIG. 13 shows TSPO binding is co-localized in activated astrocytes in regions affected by Sandhoff disease. Representative micrographs showing TSPO binding via high-resolution [$^3$H]-(R)-PK11195 emulsion autoradiography as indicated by silver grain density in conjunction with GFAP immunohistochemistry to determine the cellular localization of TSPO binding. Wildtype mice showed little to no silver grain nor detection of activated astrocytes in thalamus (FIG. 13A), cerebellum (FIG. 13D), and brainstem (FIG. 13G). Sandhoff mice showed increased silver grain density, indicative of increased TSPO binding, co-localized in activated astrocytes in the thalamus (FIG. 13B), cerebellum (FIG. 13E), and brainstem (FIG. 13H). The increased binding in Sandhoff mice appeared to be specific as high concentration of nonradiolabeled PK11195 competed with [$^3$H]-(R)-PK11195 binding (FIG. 13C for thalamus, FIG. 13F for cerebellum, and FIG. 13I for brainstem). Scale bar=10 μm.

Figure 14:
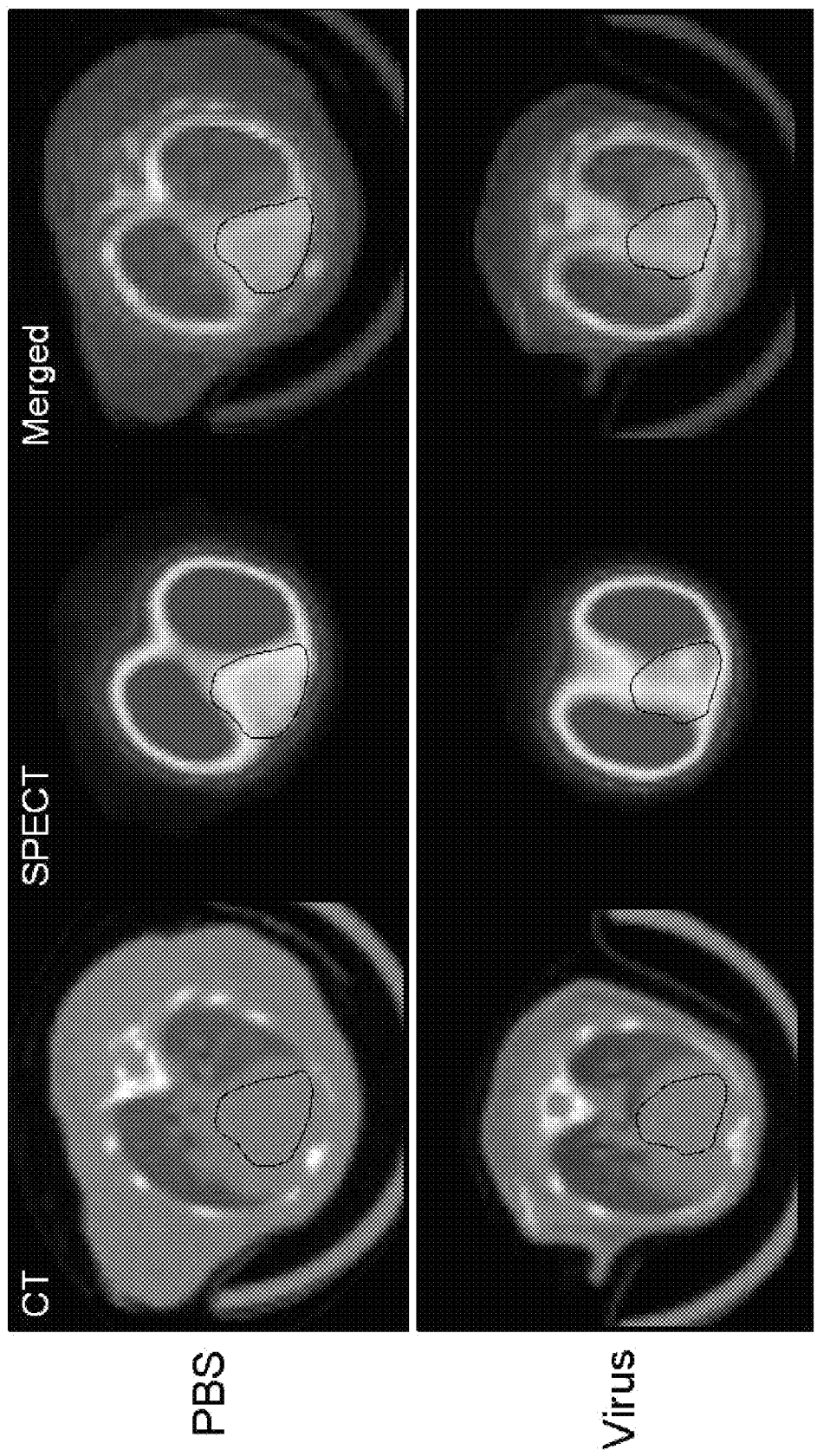

FIG. 14 shows in vivo microSPECT imaging showing higher uptake of [$^{125}$I]-IodoDPA-713 in the heart of a mouse model of acute coxsackievirus-induced myocarditis. FIG. 14 shows representative transverse slices showing the difference of [$^{125}$I]IodoDPA-713 accumulation between PBS-injected control mouse (top panel) and coxsackievirus-injected mouse (bottom panel). The CT (left), for orientation purposes, indicates that slices are at the level of the heart (solid line). Tracer uptake appears higher in the heart of coxsackievirus-injected mouse than the control mouse.

Figure 15:
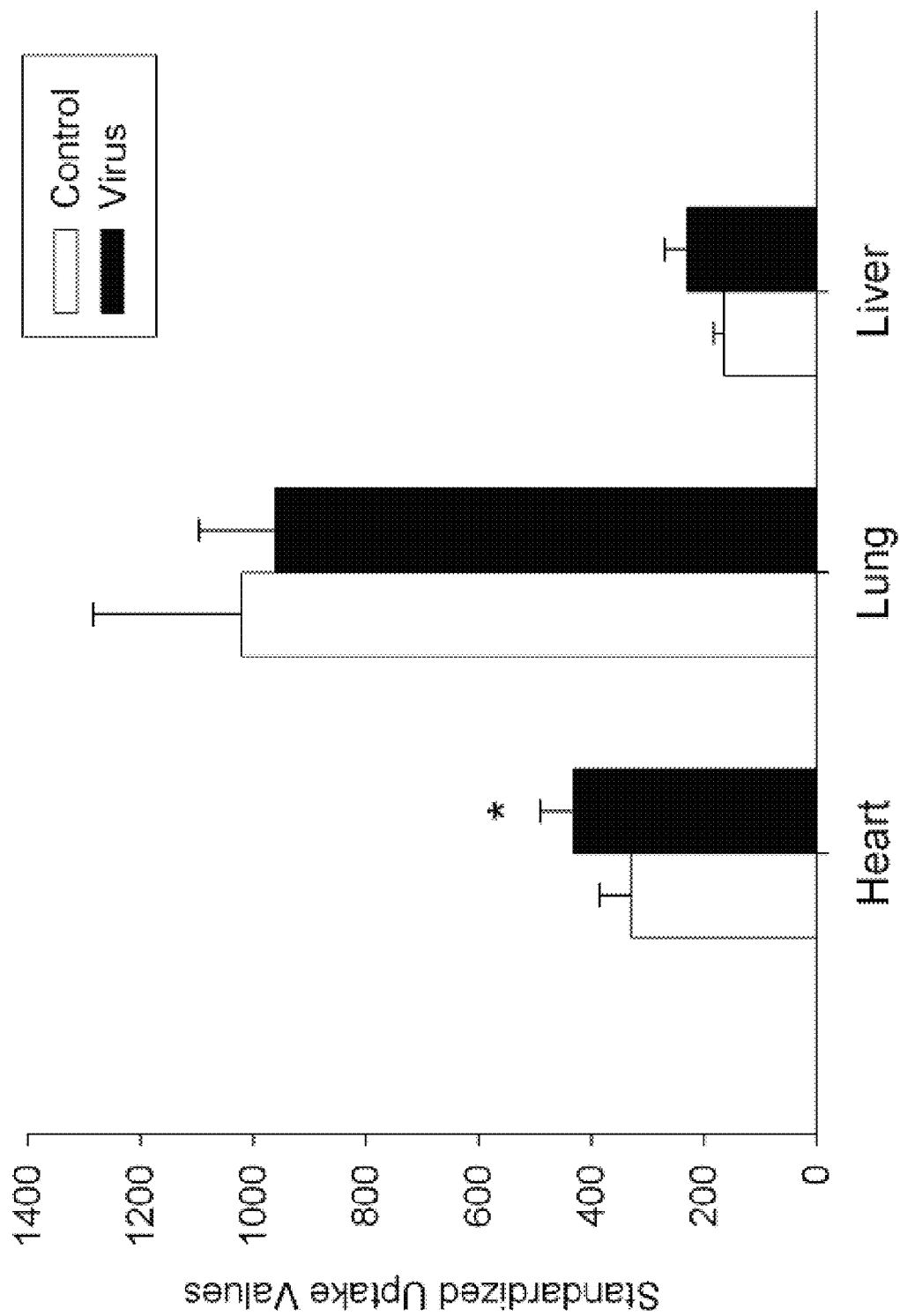

FIG. 15 shows quantitative analysis of tracer uptake demonstrating that coxsackievirus-injected mice showed a statistically significant increase of [$^{125}$I]-IodoDPA713 uptake than the PBS-injected control mice. The tracer uptake in the lungs and liver were also analyzed to indicate that the increased [$^{125}$I]-IodoDPA-713 uptake is heart-specific. Images are expressed in units of standardized uptake values (SUV) and are normalized for weight and injected dose. Data is expressed as the mean of SUV±SEM (n=3 male mice per group, *p<0.05 compared to control using a paired t-test).

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Where a range of values is provided in the present application, it is understood that each intervening value, to the tenth of the unit of the lower limit unless the context clearly dictates otherwise, between the upper and lower limit of that range and any other stated or intervening value in that stated range, is encompassed within the invention. The end values of any range are included in the range.

DEFINITIONS

The following terms below generally have the meaning that would be readily understood by persons skilled in the art. The definitions are provided herein for clarity. Where a definition excludes an art-recognized meaning, the term should be taken to have the meaning set forth below. Where the art-recognized meaning and the meaning below differ but are not exclusive, the intended meaning is clear by the context in which it is used.

As used herein, "agent" is a non-peptide, small molecule compound.

By "control" is meant a standard or reference condition.

By "disease" is meant any condition or disorder that damages or interferes with the normal function of a cell, tissue, organ or subject.

By "effective amount" is meant a quantity sufficient to produce a measurable difference, when compared with a control. For example, an amount sufficient to produce a measurable image, when the compound is used for imaging. Ultimately, the attending clinician will decide the appropriate amount and dosage regimen.

By "subject" is meant a mammal, including, but not limited to, a human or non-human mammal, such as a primate, rodent, bovine, equine, canine, ovine, or feline.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

Compounds

Embodiments of the invention include compounds having the structure

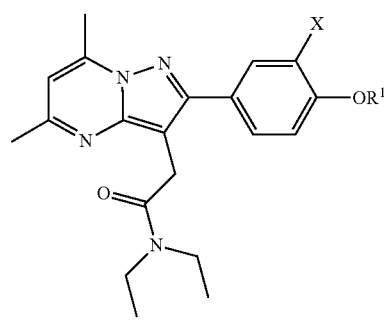

where X is H, I, $^{123}$I, $^{124}$I, $^{125}$I, or $^{131}$I, and R$^1$ is H or CH$_3$, with the proviso that when X is H, R$^1$ is not CH$_3$. In other words, the compound

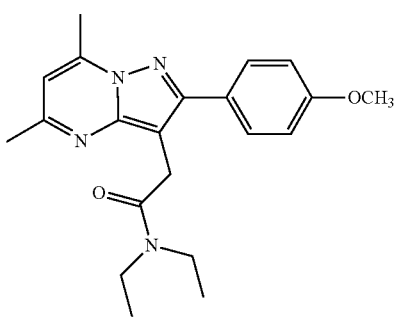 [SMILES: CCN(CC)C(=O)Cc1c(-c2ccc(OC)cc2)nn2c(C)cc(C)nc12]

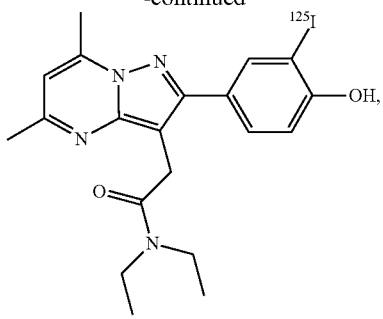

is excluded.

Embodiments of the invention include compounds having the structure

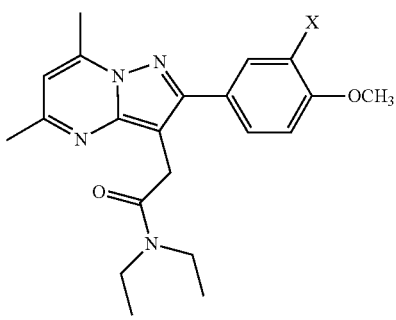

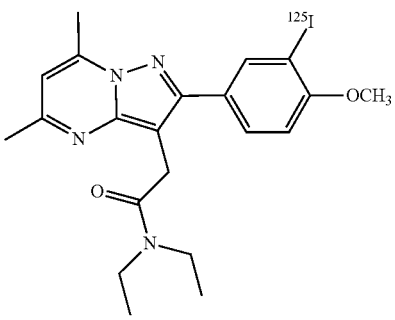

where X is I, $^{123}$I, $^{124}$I, $^{125}$I, or $^{131}$I. Further embodiments of the invention include any of the above compounds isotopically enriched in one of $^{123}$I, $^{124}$I, $^{125}$I, or $^{131}$I. As used herein, "isotopically enriched," means that the amount of $^{123}$I, $^{124}$I, $^{125}$I, or $^{131}$I is greater than the natural abundance. The isotopically enriched compound is not necessarily 100% enriched. One of ordinary skill understands that 100% enrichment is impractical and unlikely. The percent enrichment should be sufficient to be detected using radioimaging methods. The amount of enrichment may also be expressed by specific radioactivity, or units of radioactivity per mol, for example GBq/μmol, or Ci/mmol, or variation thereof. The specific radioactivity will vary based on the isotope used. The specific radioactivity should be sufficient to be detected using radioimaging methods.

In some embodiments, the compound may have one of the structures shown below.

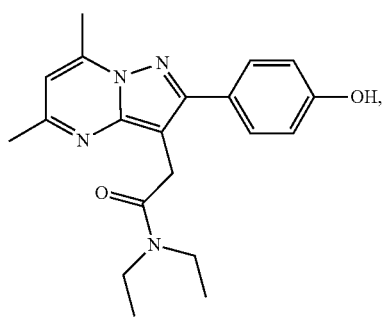

Uses

Compounds described above, including various radiolabeled compounds, may be used for diagnostic or imaging purposes. In general, the suitability of a particular radioisotope for a particular purpose (i.e. imaging) is well understood in the art. Other embodiments are compounds used as precursors for radiolabeled compounds. Some compounds according to the invention are intermediates for forming other compounds of the invention.

Preparation

The compounds described in the above embodiments may be made using procedures known in the art, for example, according to the process described below and in Example 1.

Embodiments include methods for preparing compounds having the structure

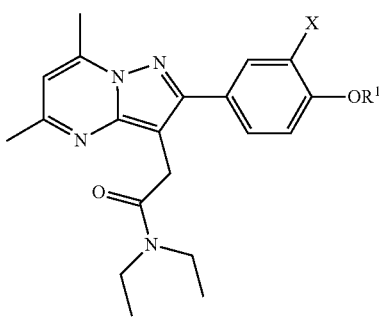

where X is I, $^{123}$I, $^{124}$I, $^{125}$I, or $^{131}$I; and R$^1$ is H or CH$_3$, by reacting, in part, a compound of the structure

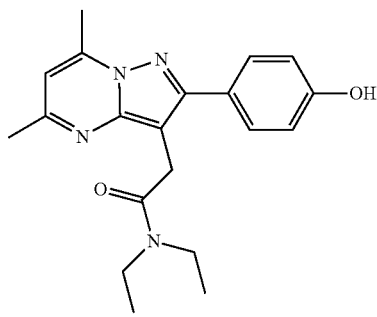 [SMILES: CCN(CC)C(=O)Cc1c(-c2ccc(O)cc2)nn2c(C)cc(C)nc12]

with iodide in the presence of iodogen or chloramine-T, where the iodide may be isotopically enriched in one of $^{123}$I, $^{124}$I, $^{125}$I, or $^{131}$I. As used herein, "iodide" means the anion of iodine (I$^-$), and is associated with a counterion. Any suitable counterion may be used, including but not limited to alkali metal cations, alkaline earth metal cations, and substituted amine cations. In some embodiments, the iodide is sodium iodide (NaI), or isotopically enriched forms thereof. The reaction may be performed in any suitable solvent, including water, organic solvent or mixtures thereof. Organic solvents include, for example, acetonitrile (CH$_3$CN) or methanol (CH$_3$OH), or mixtures thereof.

The method may further include reacting

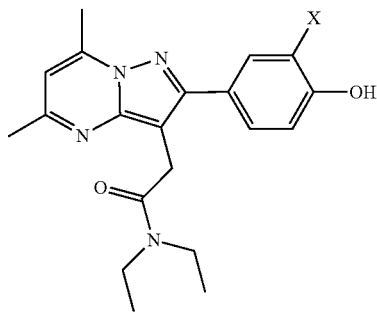

where X is I, $^{123}$I, $^{124}$I, $^{125}$I, or $^{131}$I with a methylating agent. The product of the reaction has the structure

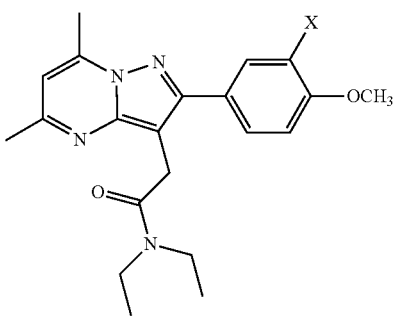

where X is I, $^{123}$I, $^{124}$I, $^{125}$I, or $^{131}$I. Any methylating reagents that reacts with the phenol hydroxyl without reacting with other portions of the molecule may be used. Many methylating reagents are known, such as, for example methyl iodide, dimethyl sulfate, dimethyl carbonate, methyl trifluoromethanesulfonate, or methyl fluorosulfonate. In some embodiments, the methylating agent is methyl iodide. The reaction may also include a base. Any base may be used that does not otherwise interfere with the reaction. Examples include carbonate (CO$_3$$^{2-}$), associated with a suitable cation, such as potassium (K$^+$) or sodium (Na$^+$). In some embodiments, the base is potassium carbonate (K$_2$CO$_3$).

Imaging

[$^{11}$C]-DPA-713 has been used previously for in vivo PET imaging in rodent models of neuroinflammation and brain injury (Boutin et al., J. Nucl. Med., vol. 48, pp. 573-581, 2007; Doorduin et al., Mol. Imag. Biol., vol. 11, no. 6, pp. 386-398, 2009) as well as in humans (Endres et al., J. Nucl. Med., vol. 50, pp. 1276-1282, 2009). Consistently, [$^{11}$C]-DPA-713 imaging showed higher brain uptake and better signal-to-noise ratio than [$^{11}$C]-PK11195 (James et al., Bioorg. Med. Chem., vol. 13, pp. 6188-6194, 2005; Boutin et al., J. Nucl. Med., vol. 48, pp. 573-581, 2007), suggesting that DPA-713 is a promising ligand for TSPO imaging. Both PET and SPECT imaging can detect small amounts of radiotracers in vivo, PET imaging can prove to be extremely time sensitive because of the half-lives of PET radionuclides such as [$^{11}$C] (20 minutes) and [$^{18}$F] (109 minutes) (Meikle et al., Phys. Med. Biol., vol. 50, no. 22, pp. R45-R61, 2005). PET imaging is also limited to the availability of a cyclotron on site, which, in conjunction with the short half-lives of the radionuclide, can be difficult and costly for small animal imaging (Wang et al., Biochem. Biophy. Res. Comm., vol. 389, no. 1, pp. 80-83, 2009). On the other hand, syntheses of SPECT radioligands such as iodination of tracers are easier than syntheses of PET radioligands, and the half-lives of radionuclides such as [$^{125}$I] (59 days) are much longer (Meikle et al., Phys. Med. Biol., vol. 50, no. 22, pp. R45-R61, 2005).

Embodiments include methods for imaging cells, tissues, a sample, an organ or a subject by imaging the cells, the tissues, a sample, an organ or a subject which has or is suspected of having increased levels of translocator protein, TSPO, after administration of a detectably sufficient amount of a radioisotopically-enriched compound having the structure

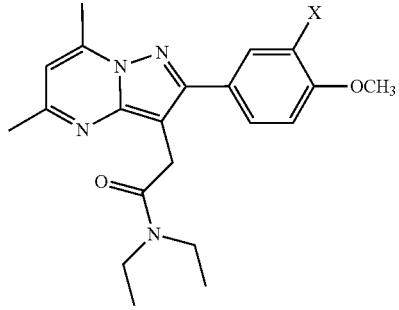

where X is $^{123}$I, $^{124}$I, $^{125}$I, or $^{131}$I. The method may further include administering, before imaging, a detectably sufficient amount of a radioisotopically-enriched compound having the structure

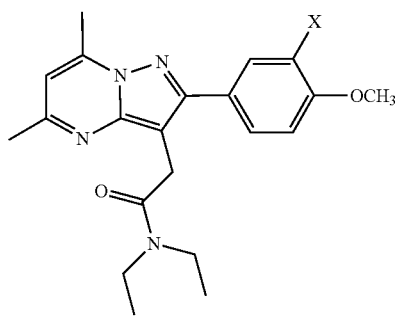

where X is $^{123}$I, $^{124}$I, $^{125}$I, or $^{131}$I. As will be appreciated, the isotope chosen will depend upon the imaging technique to be used.

The image indicates the level of TSPO protein, relative to the background. Regions of increased TSPO protein may be visualized by comparing them with the background level of TSPO protein in a particular culture, sample, organ, or subject. The background may be produced, for example, by non-specific binding of the compound to other proteins. TSPO protein levels below the level of detection will not be imaged. Likewise, TSPO levels below the level of background will not be imaged. Compounds of the invention are highly specific for TSPO, have minimal non-specific binding, and therefore a low background. Increased TSPO may be caused by increased expression of TSPO protein in the cells, tissues, sample, organ or subject being imaged. In other instances, TSPO protein may be produced elsewhere and migrate to the imaged cells, sample, organ or subject. Where elevated levels of TSPO are associated with cells, tissues, samples or organs, they may be imaged using the compounds and methods of the invention.

Embodiments include methods of imaging one or more cells, organs, tissues, samples or subjects by exposing cells to or administering to a subject a detectably effective amount of a compound with an isotopic label suitable for imaging. The cells, organs, tissues or samples may be imaged while within an organism, either by whole body imaging or intraoperative imaging, or may be excised from the organism for imaging.

Cells may be imaged, for example, in culture, in a tissue, organ, or even in a subject. Cells may be imaged collectively. Cells or a sample may imaged be in vivo or in vitro, and may be, for example, a sample of an organ or other portion of an organism, or tissue samples grown in culture. In some cases, the sample may be removed from an organism prior to imaging. In some embodiments, organs or portions of organs may be removed prior to imaging, or imaged in vivo. Imaging organs means detecting or visualizing the organ, or portion of the organ associated with elevated levels of TSPO protein. In some inflammation, TSPO may be expressed by immune cells associated with the inflamed organ or tissue, but imaging these cells produces an image of the inflamed portion of the organ itself. All such uses are envisioned.

Imaging includes, for example, autoradiography, single photon emission computed tomography, or positron emission tomography. Different isotopes may be used for different types of imaging, as known in the art. In some embodiments, the imaging is autoradiography. In some embodiments, imaging is single photon emission computed tomography (SPECT) and the compound is radioisotopically-enriched with $^{123}$I or $^{125}$I. In some instances, SPECT is associated with computed tomography (CT) to produce a hybrid image by SPECT-CT. In some embodiments, the imaging is positron emission tomography (PET) and the compound is radioisotopically-enriched with $^{124}$I.

In general, any cells expressing or overexpressing TSPO may be imaged. In some embodiments, the cells are glial cells or immune cells. Glial cells include, for example, microglia, astrocytes, oligodendrocytes, ependymal cells or ependymocytes, radial glia, and Schwann cells. Immune cells include, for example, macrophages, monocytes, leukocytes, and lymphocytes. Other cells that may express or overexpress TSPO include, for example, steroidogenic cells such as testicular, adrenocortical, and brain glial tumor cells, and cancerous tissues of the breast, ovary, colon, prostate, and brain.

In some embodiments, the organ being imaged is the brain. In some embodiments, the organ being imaged is the lungs. In some embodiments, the organ being imaged is the heart. In other embodiments, organs (e.g. spleen) and tissues of the lymphatic system may be imaged.

In general, any condition associated with TSPO expression may be imaged in a subject. In some embodiments, the subject has inflammation. In some embodiments, the subject has an autoimmune disease. In some embodiments, the subject has inflammatory arthritides. In some embodiments, the subject has a neurodegenerative disease. In some embodiments, the subject has atherosclerosis. Other conditions that may be associated with TSPO expression include neuropathological conditions including stroke, herpes and HIV encephalitis, and neurodegenerative disorders such as Alzheimer's disease, multiple sclerosis, amyotrophic lateral sclerosis, Parkinson's disease, and Huntington's disease, and other conditions such as myocarditis, pneumonitis, and pneumonia.

In some embodiments, the subject is a human, rat, mouse, cat, dog, horse, sheep, cow, monkey, avian, or amphibian. In another embodiment, the cell is in vivo or in vitro. Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood, urine or tissue samples of the animals mentioned for veterinary applications. In other in vitro applications, the cells or tissues are present in culture or in suspension.

Imaging agents of the invention may be used in accordance with the methods of the invention by one of skill in the art. Images can be generated by virtue of differences in the spatial distribution of the imaging agents which accumulate at a site when contacted with TSPO. The spatial distribution may be measured using any means suitable for the particular label, for example, a gamma camera, a PET apparatus, a SPECT apparatus, and the like. The extent of accumulation of the imaging agent may be quantified using known methods for quantifying radioactive emissions.

In general, a detectably effective amount of the imaging agent is administered to a subject. As used herein, "a detectably effective amount" of the imaging agent is defined as an amount sufficient to yield an acceptable image using equipment which is available for clinical use. A detectably effective amount of the imaging agent may be administered in more than one dose. The imaging agent can be administered in any suitable to result in delivery to the site where TSPO accumulation may be expected to occur. Examples of administration include ingestion or injection, including, for example, interperitoneal injection or intravenous injection.

The detectably effective amount of the imaging agent can vary according to factors such as the degree of susceptibility of the individual, the age, sex, and weight of the individual, idiosyncratic responses of the individual, and the dosimetry. Detectably effective amounts of the imaging agent can also vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

In some embodiments, the compounds are excreted from tissues of the body of the subject quickly to prevent prolonged exposure to the radiation of the radiolabeled compound administered to the patient. Generally, the compounds are excreted from tissues of the body slowly enough to allow sufficient time for imaging or other use. Typically compounds of the invention are eliminated from the body in less than about 24 hours. More typically, compounds of the invention are eliminated from the body in less than about 16 hours, 12 hours, 8 hours, 6 hours, 4 hours, 2 hours, 90 minutes, or 60 minutes. Compounds may be eliminated in between about 60 minutes and about 120 minutes.

Pharmaceutical Compositions and Kits

The compounds discussed herein can be formulated into various compositions, for use in diagnostic or imaging methods. The compositions (e.g. pharmaceutical compositions) can be assembled as a kit. Generally, a pharmaceutical composition comprises an effective amount (e.g., a detectably effective amount) of a compound described above.

A composition of the invention can be formulated as a pharmaceutical composition, which comprises a compound of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^{th}$ ed., Mack Publishing Company, 1990. The pharmaceutically acceptable carrier may also contain stabilizers, preservatives, antioxidants, or other additives, which are well known to one of skill in the art, or other vehicle as known in the art. Suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

In some embodiments, "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like.

A pharmaceutical composition or kit of the invention can contain other pharmaceuticals or imaging agents, in addition to the compounds described herein. The other agent(s) can be administered at any suitable time during the imaging process, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

One skilled in the art will appreciate that a suitable or appropriate formulation can be selected, adapted or developed based upon the particular application at hand. Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a composition of the invention, administered to an animal, particularly a human, in the context of the present invention should be sufficient to produce at least a detectable amount of a diagnostic or imaging response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Other embodiments provide kits including a compound according to the invention. In certain embodiments, the kit provides packaged pharmaceutical compositions having a pharmaceutically acceptable carrier and a compound of the invention. In some embodiments the packaged pharmaceutical composition will include the reaction precursors necessary to generate the compound of the invention upon combination with a radionuclide. Other packaged pharmaceutical compositions provided by the present invention further include indicia such as at least one of: instructions for preparing compounds according to the invention from supplied precursors, instructions for using the composition to image cells or tissues expressing TSPO, or instructions for using the composition to image inflammation or neurodegeneration in a patient suffering, for example, an autoimmune disease, an inflammatory arthritides, a neurodegenerative disease, or atherosclerosis.

In certain embodiments, a kit according to the invention may contain, for example, from about 1 mCi to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. The kit may provide a compound of the invention in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form. Determination and optimization of such stabilizers and stabilization methods are well within the level of skill in the art.

The contents of all cited references (including literature references, issued patents, published patent applications) as cited throughout this application are hereby expressly incorporated by reference. The invention and the manner and process of making and using it, are described in such full, clear, concise and exact terms as to enable any person skilled in the art to which it pertains, to make and use the same.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

It is to be understood that the foregoing describes exemplary embodiments of the present invention and that modifications may be made therein without departing from the spirit or scope of the present invention as set forth in the appended claims.

EXAMPLES

The present invention is further illustrated by the following examples which should not be construed as limiting in any way. The practice of the present invention will employ, unless otherwise indicated, conventional techniques, which are within the skill of the art. Such techniques are explained fully in the literature.

General

Chemicals and solvents obtained from commercial sources were analytical grade or better and used without further purification. Iodine-125 ($^{125}$I) was obtained as a 0.1 N solution of NaOH (high concentration) from MP Biomedicals (Solon, Ohio). Analytical thin-layer chromatography (TLC) was performed using Aldrich aluminum-backed 0.2 mm silica gel plates and visualized by UV light (254 nm) and $I_2$. Flash column chromatography was performed on silica gel (60 Å) from MP Biomedicals. Radio-HPLC purification was performed using a Waters (Milford, Mass.) system consisting of two Waters 510 pumps, a Waters 490E variable wavelength UV/Vis detector set at 254 nm, a BioScan FlowCount radioactivity detector, a Waters radial-PAK $C_{18}$ reverse phase analytical column (8×100 mm) with $H_2O/CH_3CN/TFA$ solvent systems, and WinFlow (LabLogic) chromatography software. $^1$H NMR was recorded on a Bruker (Billerica, Mass.) Ultrashield™ 400 MHz spectrometer. ESI mass spectra were obtained with a Bruker Daltonics Esquire 300 plus spectrometer. Radioactivity was measured in a Capintec CRC-12 dose calibrator. The specific radioactivity was calculated as the radioactivity eluting at the retention time of [$^{125}$I]1 during HPLC purification divided by the mass corresponding to the area under the curve of UV absorption.

Example 1

Chemical Synthesis

N,N-Diethyl-2-[2-(3-iodo-4-methoxyphenyl)-5,7-dimethylpyrazolo[1,5-a]pyrimidin-3-yl]acetamide (iodoDPA-713) 1 was synthesized according to the scheme below in three steps from N-diethyl-2-[2-(4-methoxy-phenyl)-5,7-dimethylpyrazolo[1,5-a]pyrimidin-3-yl]-acetamide 2 (DPA-713) (Wang et al., Biochem. Biophy. Res. Comm. Vol. 389, no. 1, pp. 80-83). Compound 2 was prepared by the procedure of James et al. (James et al., Bioorg. Med. Chem., vol. 13, pp. 6188-6194, 2005). Attempts were made to iodinate 2 directly to 1 using NaI and N-chlorosuccinimide or chloramine-T as oxidants in acidic solvents (concentrated trifluoroacetic acid or trifluoromethanesulfonic acid). However, those conditions produced no or extremely low yields of 1. Consequently, 2 was demethylated by reaction with $BBr_3$ in methylene chloride to form the more reactive phenol derivative N,N-diethyl-2-[2-(4-hydroxy-phenyl)-5,7-dimethyl-pyrazolo[1,5-a]pyrimidin-3-yl]-acetamide 3. Compound 3 was smoothly iodinated using NaI with chloroamine-T to form N,N-diethyl-2-[2-(4-hydroxy-3-iodophenyl)-5,7-dimethylpyrazolo[1,5-a]pyrimidin-3-yl]acetamide 4. Finally, O-methylation of 4 gave 1, which could then serve as the cold standard for high-performance liquid chromatography (HPLC) for radiosynthesis.

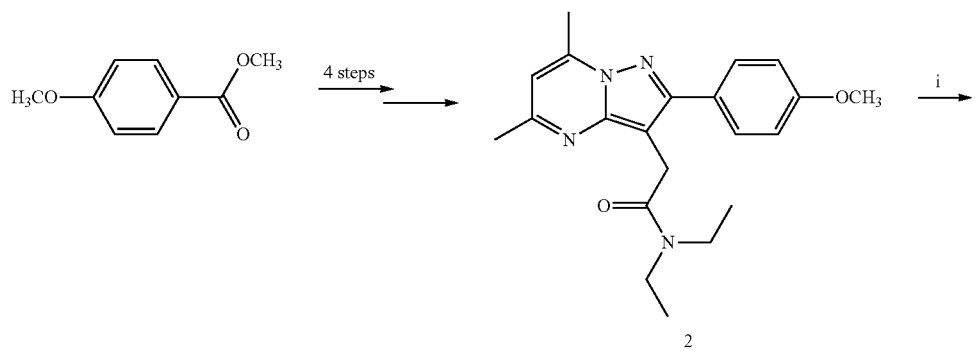

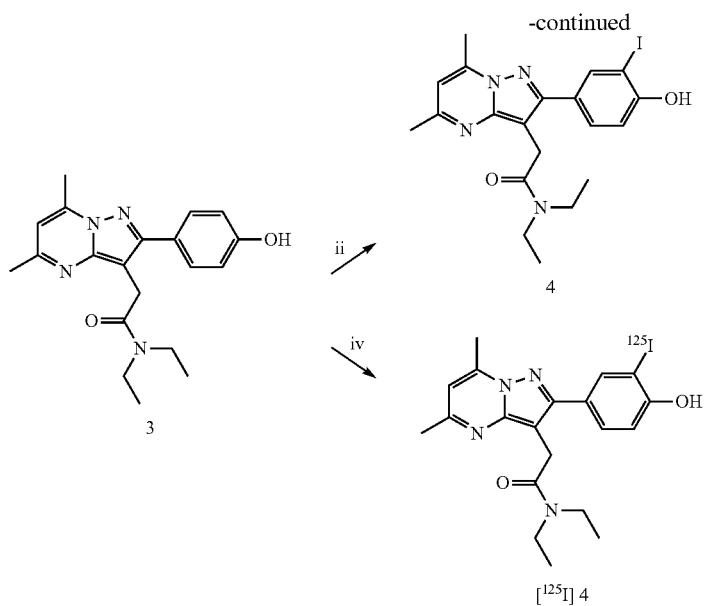
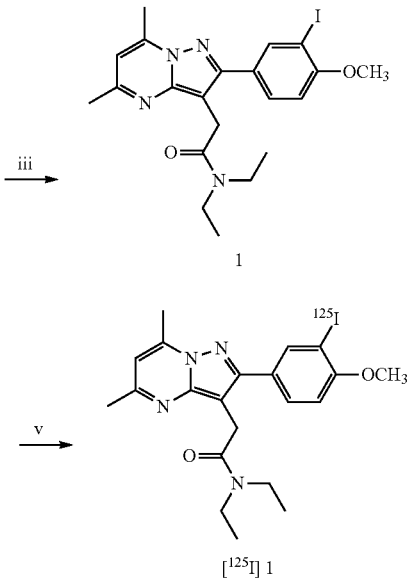

N,N-Diethyl-2-[2-(4-hydroxy-phenyl)-5,7-dimethyl-pyrazolo[1,5-a]pyrimidin-3-yl]acetamide (3). BBr$_3$ in CH$_2$Cl$_2$ (3 mL, 3 mmol) was added dropwise to a solution of 2 (0.22 g, 0.58 mmol) in CH$_2$Cl$_2$ at $-78°$ C. After stifling overnight the pH of the reaction mixture was adjusted to pH 8-9 using NaHCO$_3$ and extracted with CH$_2$Cl$_2$. The organic layer was collected and dried over anhydrous Na$_2$SO$_4$. The solvent was removed under vacuum and the residue was purified by silica gel column chromatography (CHCl$_3$/MeOH, 40:1 (v/v), as eluent) to yield 3 (0.18 g, 85%). $^1$H NMR (CDCl$_3$, 400 MHz) δ1.06-1.18 (m, 6H), 2.54 (s, 3H), 2.73 (s, 3H), 3.34-3.51 (m, 4H), 3.96 (s, 2H), 6.49 (s, 1H), 6.79-6.82 (d, J=8.7 Hz, 2H), 7.61-7.64 (d, J=8.4 Hz, 2H). ESI MS m/z: [M+H]$^+$. C$_{20}$H$_{25}$N$_4$O$_2$: calculated 353.2. found 353.2.

N,N-Diethyl-2-[2-(4-hydroxy-3-iodophenyl)-5,7-dimethylpyrazolo[1,5-a]pyrimidin-3-yl]acetamide (4). To a solution of 3 (100 mg, 0.28 mmol) in MeOH (15 mL) was added NaI (52 mg, 0.35 mmol) and chloroamine-T hydrate (80 mg, 0.35 mmol). The reaction mixture was stirred for 1 h and then concentrated under vacuum. The residue was purified by column chromatography (CH$_2$Cl$_2$/MeOH, 20:1 (v/v), as eluent) to yield 4 (60 mg, 45% yield). $^1$H NMR (CD$_3$OD, 400 MHz) δ 1.16 (t, J=7.2 Hz, 3H), 1.29 (t, J=7.2 Hz, 3H), 2.57 (s, 3H), 2.76 (s, 3H), 3.44 (q, J=7.2 Hz, 2H), 3.59 (q, J=7.2 Hz, 2H), 3.97 (s, 2H), 6.80 (s, 1H), 6.92 (d, J=8 Hz, 1H), 7.57 (d, J=8 Hz, 1H), 8.01 (s, 1H). ESI MS m/z: [M+H]+. C$_{20}$H$_{24}$IN$_4$O$_2$: calculated 479.1. found 479.1.

N,N-Diethyl-2-[2-(3-iodo-4-methoxyphenyl)-5,7-dimethylpyrazolo[1,5-a]pyrimidin-3-yl]acetamide (iodoDPA-713) (1). To a solution of 4 (30 mg, 0.063 mmol) in DMF (5 mL) was added K$_2$CO$_3$ (300 mg, 2.2 mmol) and MeI (100 μL×2M, 0.2 mmol). The reaction was stirred overnight and the solvent was removed under vacuum and the residue was purified by silica gel column chromatography (EtOAc as eluent) to give 1 (29 mg, 0.60 mmol, 95%). $^1$H NMR (CD$_3$OD, 400 MHz) δ 1.15 (t, J=7.2 Hz, 3H), 1.29 (t, J=7.2 Hz, 3H), 2.57 (s, 3H), 2.77 (s, 3H), 3.43 (q, J=7.2 Hz, 2H), 3.58 (q, J=7.2 Hz, 2H), 3.92 (s, 3H), 3.97 (s, 2H), 6.80 (s, 1H), 7.06 (d, J=8 Hz, 1H), 7.74 (d, J=8 Hz, 1H), 8.09 (s, 1H). ESI MS m/z: [M+H]$^+$ C$_{21}$H$_{26}$IN$_4$O$_2$: calculated 493.1. found 493.1.

Radiochemical Synthesis

The synthesis of [$^{125}$I]1 proceeded with an average radiochemical yield of 44±6% by reaction of 3 with iodogen (scheme above) followed by methylation of the radioiodinated product. Compound [$^{125}$I]1 was produced in specific radioactivities of 51.8 GBq/μmmol (1400 mCi/lmol) in >99% radiochemical purity.

Figure 1:
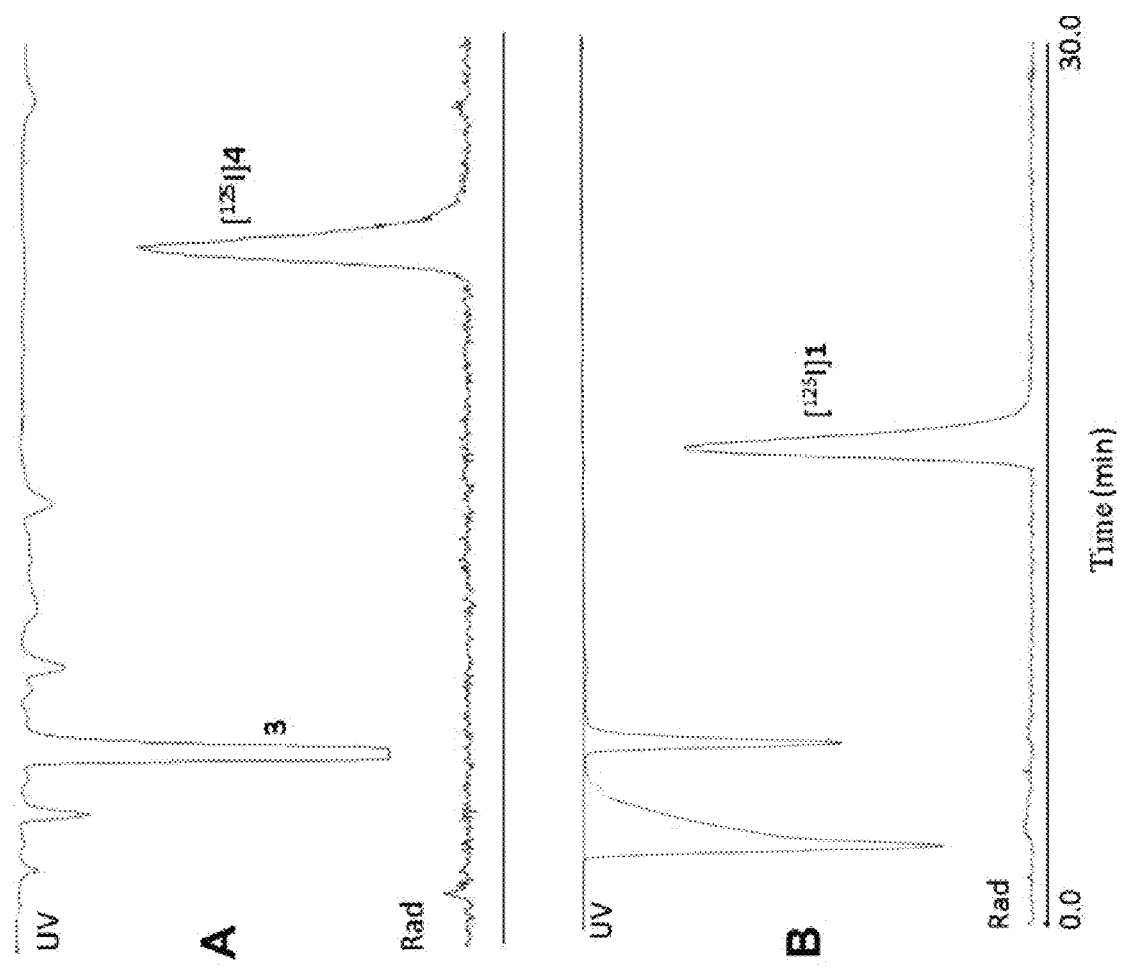
FIG. 1 shows High-performance liquid chromatography (HPLC) traces in the synthesis of N,N-Diethyl-2-[2-(4-hydroxy-3-[$^{125}$I]-iodophenyl)-5,7-dimethylpyrazolo[1,5-a]pyrimidin-3-yl]acetamide [$^{125}$I]4 from 3 (FIG. 1A) and [$^{125}$I] iodoDPA-713 ([$^{125}$I]1) (FIG. 1B). Retention times for [$^{125}$I]4 and [$^{125}$I]1 were 22.8 and 15.5 min, respectively. The radiochemical yield of [$^{125}$I]1 was 44±6% with a specific radioactivity of 51.8 GBq/μmol (1400 mCi/μmol) and >99% radiochemical purity.

N,N-Diethyl-2-[2-(4-hydroxy-3-[$^{125}$I]-iodophenyl)-5,7-dimethylpyrazolo[1,5-a]pyrimidin-3-yl]acetamide ([$^{125}$I]4). To a solution of 1 mg of 3 in 0.1 mL of CH$_3$CN, 0.1 mL of methanol and 0.1 mL of phosphate buffered saline was added 0.2 mg of iodogen (Pierce, Rockford, Ill.), followed by 2 mCi of [$^{125}$I]NaI. The reaction mixture was incubated at room temperature for 1.5 h and purified by reverse phase HPLC using 70% H$_2$O/30% CH$_3$CN/0.1% TFA with a flow rate of 2 mL/min on a Waters Radial-Pak analytical column (8×10 mm). The retention time of [$^{125}$I]4 was 22.8 min (FIG. 1A). The radioactive fraction corresponding to [$^{125}$I]4 was collected, diluted with water and passed through a pre-conditioned C$_{18}$ light Sep-Pak cartridge (Waters Corp, Milford, Mass.) eluted with 0.5 mL of ether. The ether was evaporated under a stream of nitrogen and the residue was used in the next step. Yield: 44% (n=3), 0.041 GBq (1.1 mCi).

N,N-Diethyl-2-[2-(3-[$^{125}$I]-iodo-4-methoxyphenyl)-5,7-dimethylpyrazolo[1,5-a]pyrimidin-3-yl]acetamide ([125I] iodoDPA-713) [$^{125}$I]1. Compound [$^{125}$I]4 0.041 GBq (1.1 mCi) was dissolved in 0.2 mL of anhydrous DMF in a 2-mL V-vial. To this was added 10 mg of K$_2$CO$_3$ followed by 10 μL of 2 M MeI. The reaction mixture was stirred overnight and diluted with 0.2 mL of water and purified by reverse phase HPLC using 50% H$_2$O/50% CH$_3$CN/0.1% TFA with a flow rate of 1 mL/min on a Waters Radial-Pak analytical column (8×100 mm). The retention time of [$^{125}$I]1 was 15.5 min (FIG. 1B). The radioactive fraction corresponding to [$^{125}$I]1 was collected, diluted with water and passed through a pre-conditioned C$_{18}$ light Sep-Pak and eluted with 0.5 mL of ethanol. Yield: 0.035 GBq (0.95 mCi), 86% from [$^{125}$I]4 and 47% from 3. Specific radioactivity was 51.8 GBq/μmol (1400 Ci/mmol).

Example 2

Imaging

In Vitro Autoradiography

Fresh-frozen brains were sectioned (20 μm) on a freezing cryostat in the horizontal plane. Brain sections were thaw-mounted onto poly-L-lysine-coated slides (Sigma) and stored at −20° C. until used. Autoradiography using [$^{125}$I]IodoDPA-713 ([$^{125}$I]1) was performed on adjacent brain sections using the following procedures. Slides were thawed and dried at 37° C. for 30 min and prewashed in 50 mM Tris-HCl buffer (pH 7.4) for 5 min at room temperature. Sections were then incubated in 1.4 nM [$^{125}$I]1 in 50 mM Tris-HCl buffer for 30 min at room temperature. For non-specific binding, adjacent sections were incubated in the presence of 10 μM racemic PK11195. The reaction was terminated by two 3 min washes in cold buffer (4° C.) and two dips in cold deionized water (4° C.). Sections were air-dried and apposed to Kodak Bio-Max MR film for 1 h. Images were acquired using the MCID image analysis software (InterFocus Imaging Ltd., Cambridge, England).

Figure 2:
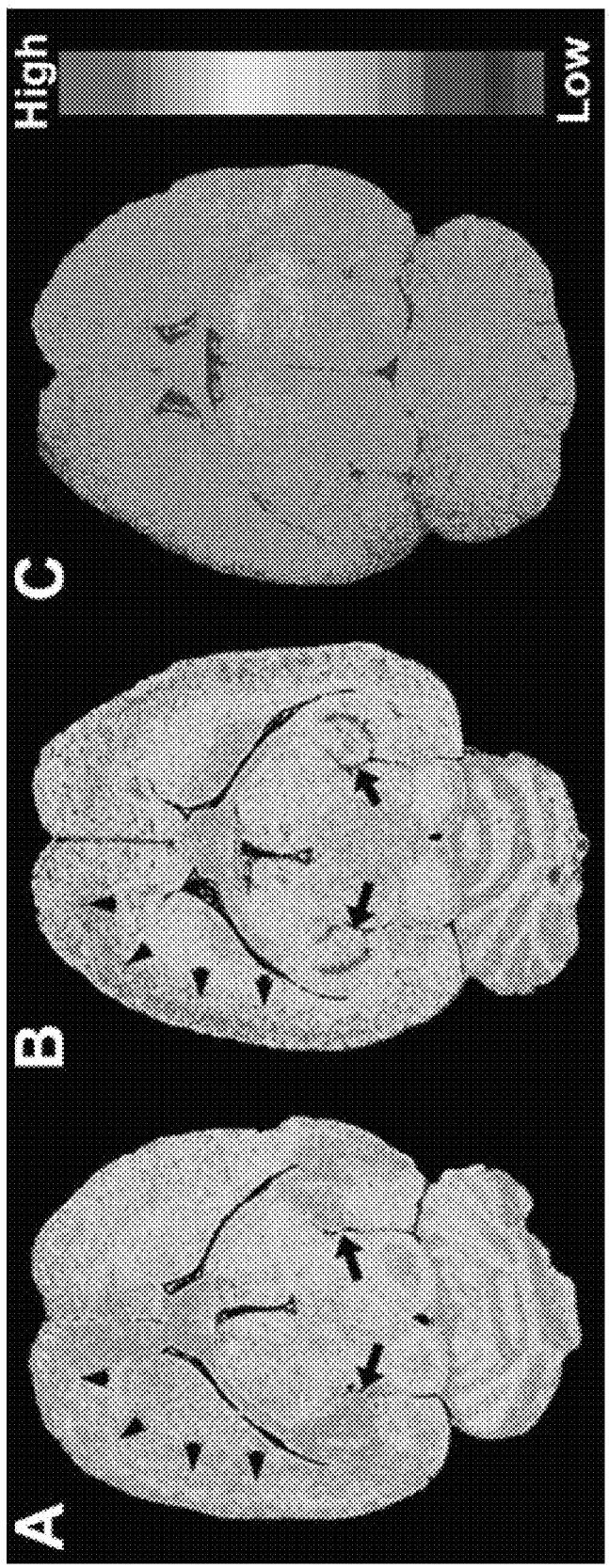
FIG. 2 shows autoradiographic images of [$^{125}$I]1 to TSPO in the rat brain. Representative horizontal images of [$^{125}$I]1 binding to TSPO in a normal rat brain (FIG. 2A) and in a neurotoxicant-injected rat brain (FIG. 2B). There is a significant increase in TSPO levels in the cerebral cortex (arrowheads) and hippocampus (arrows) in the neurotoxicantinjected rat brain (FIG. 2B) relative to the control brain (FIG. 2A). The image in FIG. 2C is representative of [$^{125}$I]1 non-specific binding using 10 μM R-PK11195 as the blocking agent in a neurotoxicant-treated rat.

The first study involved a model of brain inflammation in which rats were exposed to a seizure-inducing neurotoxicant (FIG. 2). Note that higher levels of [$^{125}$I]1 were present in the neurotoxicant-treated rat brain (FIG. 2B) than in control brain (FIG. 2A). Exposure of the tissue specimens to [$^{125}$I]1 to generate these images required only 60 min, as opposed to 4-5 weeks often needed for tritium-labeled compounds when exposing the samples to film. Rapid images can also be obtained with tritium-labeled compounds, including [$^3$H] DPA-713, using an automated system such as a Beta-Imager (Roberts et al., "Autoradiographical imaging of PPARgamma agonist effects on PBR/TSPO binding in TASTPM mice," Exp. Neurol., vol. 216, pp. 549-470, 2009), however the resolution of such images is generally inferior to that which can be obtained by exposing the tissue slices to film. Also note that uptake of [$^{125}$I]1 could be almost completely blocked in the neurotoxicant-treated rat upon treatment with PK11195 (FIG. 2C), demonstrating that most binding seen in this in vitro study was specific for TSPO.

SPECT-CT Imaging

Eight- to 10-week-old female CD-1 mice (Charles River Labs) were imaged. Mice were anesthetized by brief isoflurane sedation. While anesthetized, intranasal instillation was conducted by placing 10 μg/60 μL (167 μg/mL) of lipopolysaccharide (LPS) onto the nares (Szarka et al., "A murine model of pulmonary damage induced by lipopolysaccharide via intranasal instillation," J. Immunol. Methods, vol. 202, pp. 49-57, 1997). The 60 μL sample was applied onto the nares as three 20 μL drops. Phosphate-buffered saline (PBS) was administered in a similar fashion and used as the control.

For single photon emission computed tomography-computed tomography (SPECT-CT) imaging 18.5 MBq (500 μCi) of [$^{125}$I]1 was injected via the tail vein into the LPS and PBS treated mice and imaged 1 h later, which corresponded to 24 h after the administration of LPS or PBS. That time point was chosen since it represents the time at which there is maximum inflammation in the lungs, as determined by a time course study with histologic correlation (data not shown). Each mouse was anesthetized with isoflurane and maintained under 1-2% isoflurane in oxygen. The mouse was positioned on the X-SPECT (Gamma Medica, Northridge, Calif.) gantry and was scanned using two opposing low energy pinhole collimators (Gamma Medica) rotating through 360° in 3° increments for 20 s per increment. Images were reconstructed using LumaGem software that accompanies the X-SPECT. Immediately following SPECT acquisition, the mice were scanned by CT over a 3-cm field-of-view using a 600-μA, 50 kV beam. The SPECT and CT data were then co-registered using the X-SPECT software and displayed using AMIDE (http://amide.sourceforge.net/). Data were reconstructed using the ordered subsets-expectation maximization (OS-EM) algorithm. The signal to background ratio was calculated from the images by drawing regions of interest over the lungs (signal) and muscle, (background).

Figure 3:
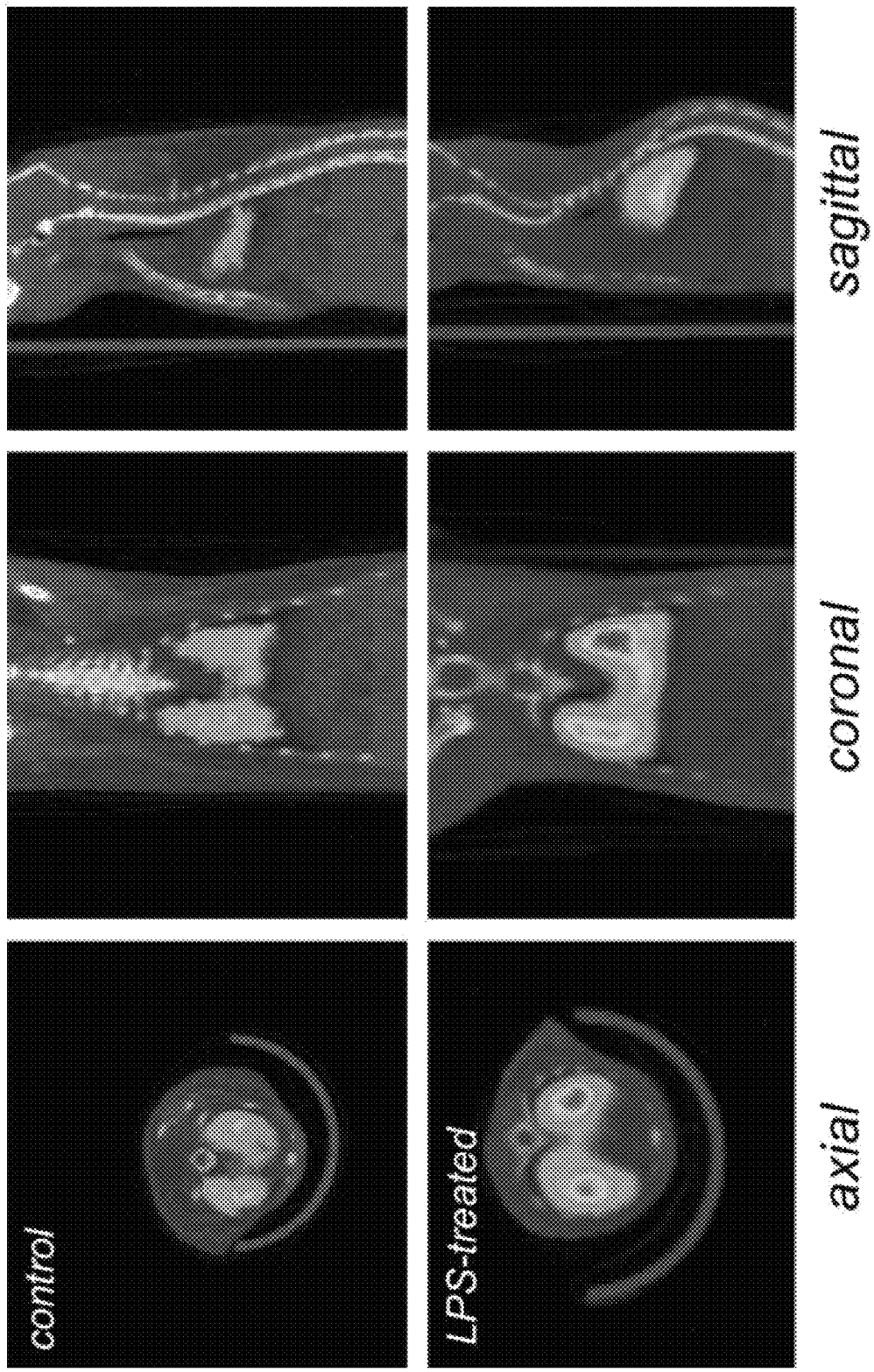
FIG. 3 shows SPECT-CT imaging of a mouse at 1 h postinjection. The lung signal to background ratio in the control mouse (top row) was 14.6 to 1 and that in the LPS treated mouse (bottom row) was 21.2 to 1.

An in vivo small animal SPECT-CT study demonstrated 1.5-fold higher uptake of [$^{125}$I]1 in inflamed mouse lungs than in normal lungs (FIG. 3). Although only one result is presented here, that was a consistent finding.

Conclusions

[$^{125}$I]IodoDPA-713 ([$^{125}$I]1) can be readily synthesized from DPA-713 in high radiochemical yield and specific radioactivity. It demonstrates specific binding to TSPO in vitro and in vivo, showing a higher level of uptake in inflamed than in the corresponding normal tissue. This agent provides a convenient and inexpensive alternative to other radiolabeled analogs of the pyrazolopyrimidine series for autoradiographic and preclinical imaging studies. Together these two studies suggest that [$^{125}$I]1 may be useful to study preclinical models of inflammation. Compound [$^{125}$I]1 is particularly relevant as it is patterned after compounds that are currently undergoing early clinical testing (Endres et al., J. Nucl. Med., vol. 50, pp. 1276-1282, 2009; Chauveau et al., J. Nucl. Med., vol. 50, pp. 468-476, 2009).

Sandhoff Disease as a Model for Neurodegenerative Imaging

Animal Model and Tissue Preparation.

Mice heterozygous for HexB were generously donated by Richard Proia (National Institute of Kidney & Digestive Diseases, Bethesda, Md.). Wildtype (HexB +/+) or Sandhoff disease (HexB −/−) mice were sacrificed at 2 months or 3 months of age and euthanized by either decapitation to obtain fresh-frozen brain tissue for receptor autoradiography or by transcardiac perfusion for immunohistochemistry. Fresh frozen brains were stored at −80° C. until used. For transcardiac perfusion, animals were deeply anesthetized with pentobarbital (100 mg/kg body weight) and perfused with 4% paraformaldehyde (PFA) in 0.1M phosphate buffer (pH 7.4 at 4° C.) or a paraformaldehyde-lysine-perioodate (PLP) solution that consisted of 2% paraformaldehyde, 75 mM L-lysine and 10 mM sodium metaperiodate in 37 mM phosphate buffer (pH 7.4 at 4° C.). The PFA solution was used to perfuse animals whose brains were used for glial fibrillary acidic protein (GFAP) or CD11b (Mac-1) immunohistochemistry or silver staining for neurodegeneration, and the PLP solution was used to perfuse animals whose brains were used for the [$^3$H]-(R)-PK11195 emulsion autoradiography in conjunction with GFAP or Mac-1 immunohistochemistry (see sections below). Perfused brains were post-fixed overnight in the same fixative, cryoprotected with 25% sucrose for at least 48 h, snap-frozen in dry-ice-cooled isopentane, and stored at −80° C. until used. All animal studies were reviewed and approved by the Johns Hopkins University Animal Care and Use Committee.

Brain and Body Weights were not Different Between Wildtype and Sandhoff Disease Mice.

Figure 4:
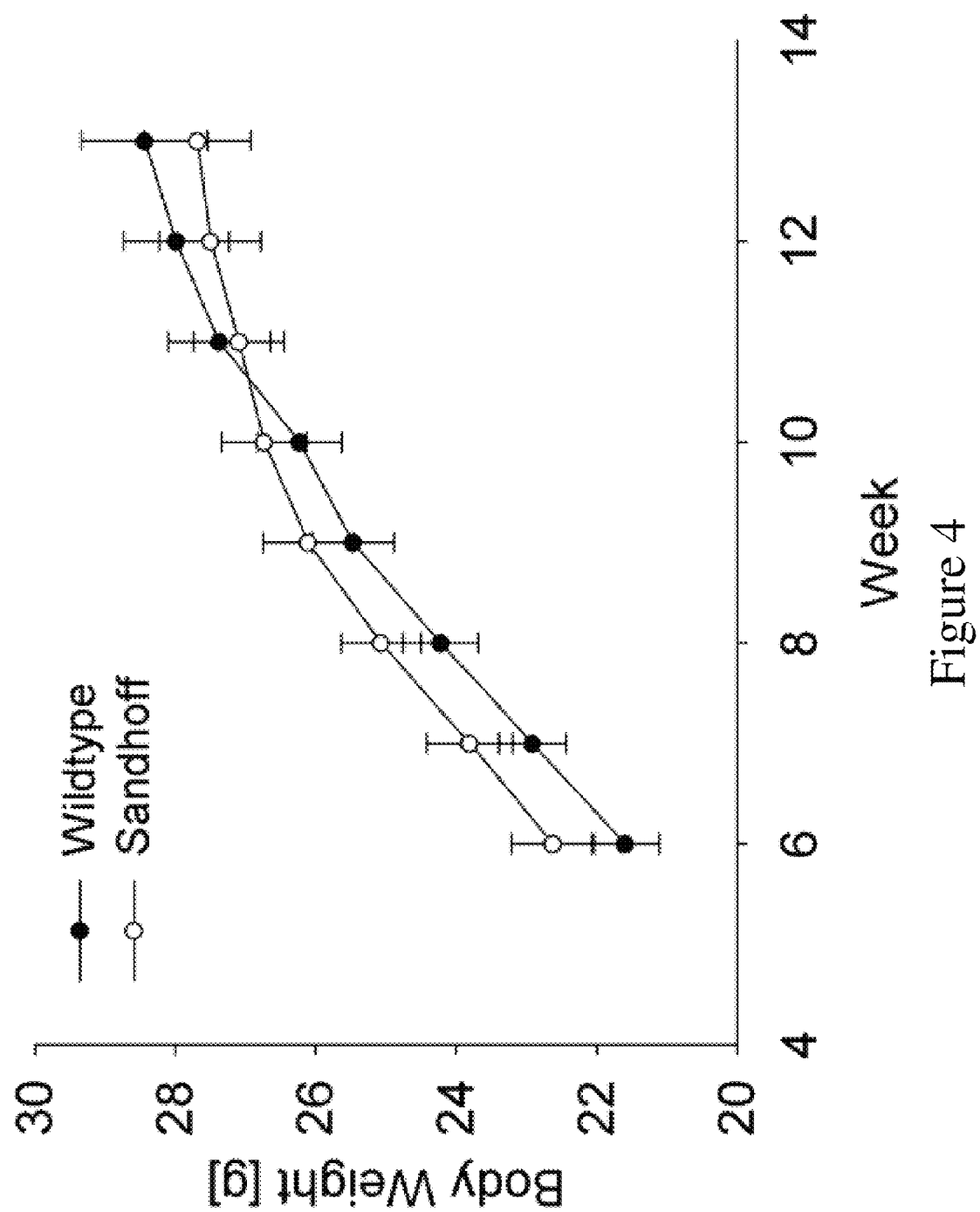
FIG. 4 shows that body weights were not different between wildtype and Sandhoff disease mice. Body weights were measured weekly for both wildtype and Sandhoff mice starting from week 6 and ending at week 13 (3 months of age). There was no significant difference of body weight between wildtype and Sandhoff mice at all time points (p=0.7295). Data is expressed as the mean of the body weights per week±SEM. n=13 for both wildtype and Sandhoff mice.

The body weights of mice were taken weekly starting at 6 weeks and ending at 13 weeks (3-month) when brains were extracted. Following extraction, the brain weights of wildtype and Sandhoff disease mice (HexB knockout) were measured at 3 months of age. Brain weights were not significantly different between wildtype (425±15.1 mg) and Sandhoff (448.4±20.3 mg) mice (data not shown). FIG. 4 shows that the body weights between wildtype and Sandhoff mice were not significantly different ($F_{1,25}$=0.12, p=0.7295).

Example 3

Behavioral Tests

Locomotor Activity.

Mice were placed in open field activity chambers with infrared beams (San Diego Instruments Inc., San Diego, Calif., USA) for 1 h, and during this time, horizontal and vertical (rearing) activities were automatically recorded.

Motor Skill.

Motor skill was measured using the rotarod apparatus (Columbus Instrument, Columbus, Ohio). The latency time that the mouse remained on the rod at accelerating speeds from 4 to 40 revolutions per minute (RPM) was recorded. Each mouse was trained for 5 min, and the training session was followed by a 30-min rest period in the home cage. Mice were then placed back on the rotarod for three trials starting at 4 RPM with accelerating speeds by 4 RPM every 30 s to a maximum of 40 RPM. Each trial was separated by a 10-min rest period. Mice were tested for 3 consecutive days when a steady baseline level of performance was attained.

Progression of Motor Function Deficits in Sandhoff Disease Mice.

It was previously shown that Sandhoff mice exhibited deterioration in motor function after 3 months of age (Sango et al., "Mouse models of Tay-Sachs and Sandhoff diseases differ in neurologic phenotype and ganglioside metabolism," Nature Genetics, vol. 11, no. 2, pp. 170-176, 1995). To gain a better understanding of the behavioral manifestation of the Sandhoff mice, motor activities of wildtype and Sandhoff mice were measured and compared by automated open field activity chambers, and motor skill was measured by a rotarod test at 2 and 3 months of age. At 2 months, Sandhoff mice exhibited a slight but significant decrease in locomotor activity (FIG. 5A-5B; $F_{1,23}=7.11$, $p=0.014$) and rearing (ability to stand on the hind legs; FIG. 5C-5D; $F_{1,23}=5.95$, $p=0.022$) over a 1 hour period. However, there was no significant difference in motor skill from the rotarod test (FIG. 6; $t_{17}=0.66$, $p=0.52$). At 3 months, Sandhoff mice showed more dramatic deficits in locomotor activity (FIG. 5E-5F; $F_{1,26}=11.08$, $p=0.0026$) and rearing (FIG. 5G-5H; $F_{1,26}=20.53$, $p<0.0001$) as well as in motor skill from the rotarod test (FIG. 6; $t_{27}=7.72$, $p<0.0001$). These findings indicate that slight motor function deficits occur as early as 2 months and exacerbate over time.

Figure 5:
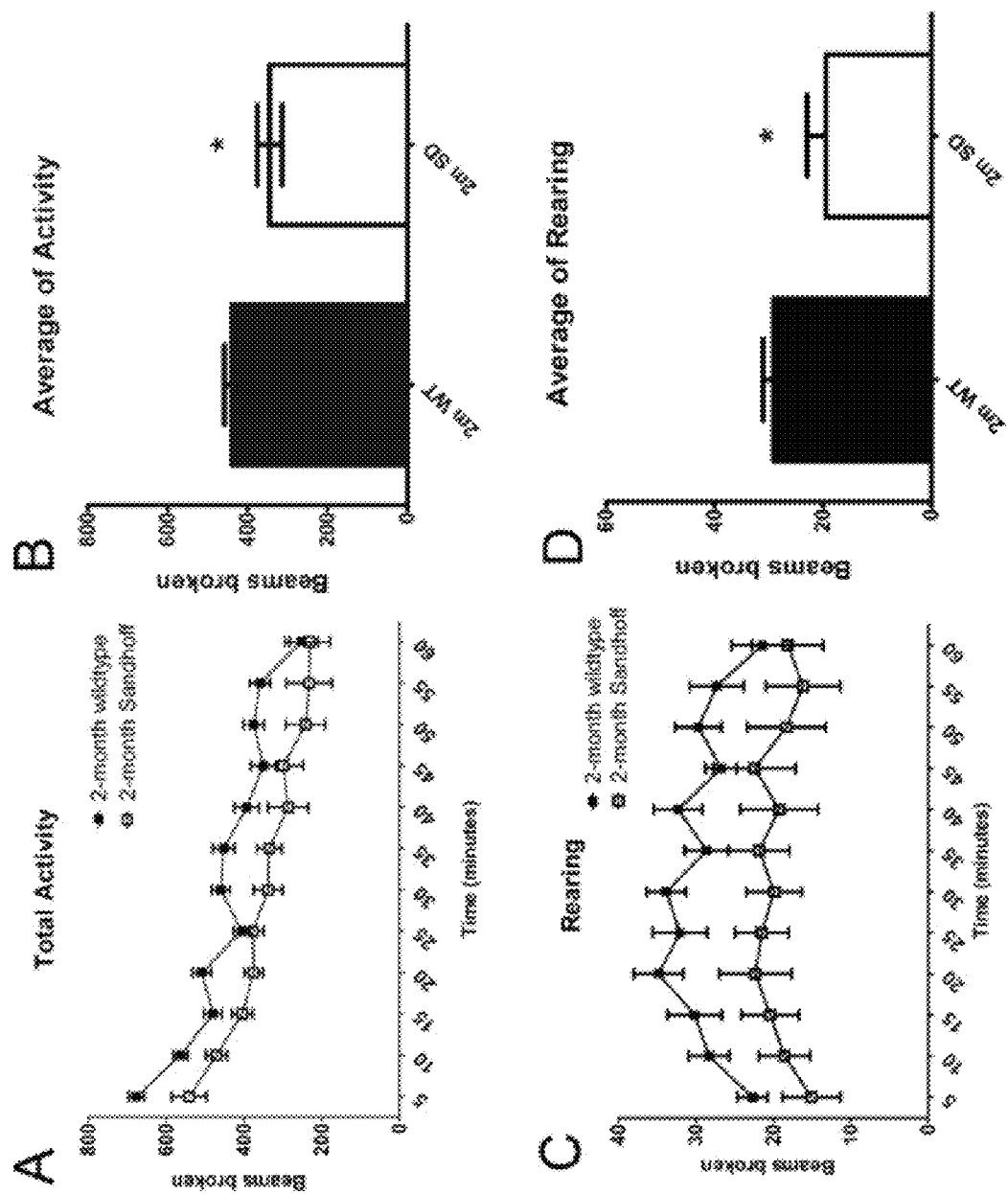
FIG. 5 shows locomotor activities of Sandhoff mice measured using the open field activity chamber at 2 months and at 3 months. At 2 months, Sandhoff mice showed a slight but statistically significant decrease in total activity (FIG. 5A) and rearing (FIG. 5C) over 1 hour period.
Figure 6:
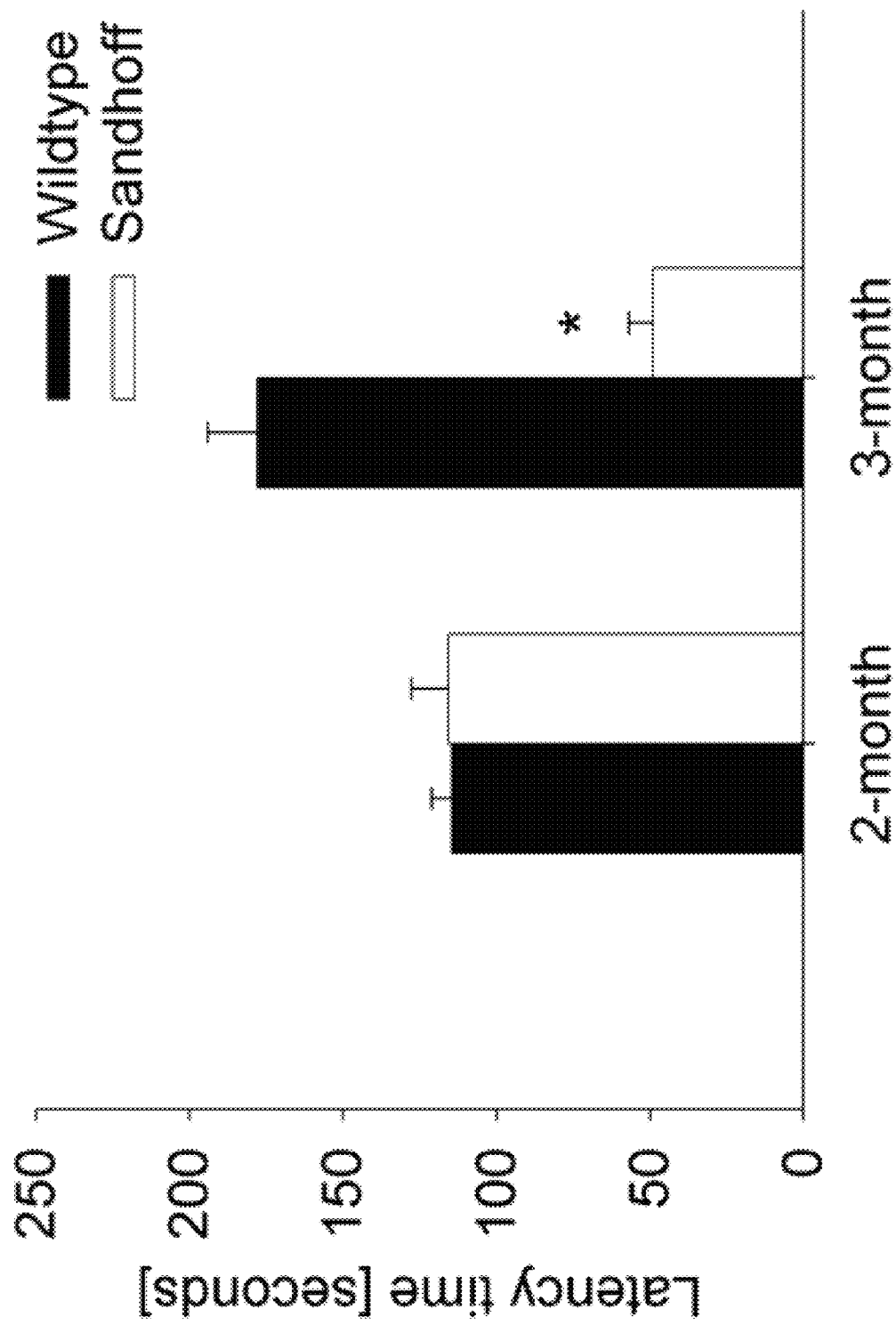
FIG. 6 shows that at 2 months, Sandhoff mice did not show deficits in motor skill, but at 3 months, Sandhoff mice showed shorter latency time, indicative of weakened motor skill Data is expressed as mean±SEM (n=11-13 male mice per group, *p<0.05 compared to wildtype).

The expression of TSPO was examined in a Sandhoff disease mouse model of neurodegeneration using a longitudinal design. Two months was defined as the time point prior to the severe behavioral expression of disease because slight function deficits were observed between wildtype and Sandhoff disease mice (FIG. 5). Later, at 3 months, significant impairments in locomotor activities and motor skills were prominent between wildtype and Sandhoff mice (FIGS. 5 and 6). This is consistent with other reports on the behavioral expression of this disease in mice (Sango et al., Nature Genetics, vol. 11, no. 2, pp. 170-176, 1995; Wada et al., Proc. Natl. Acad. Sci. USA, vol. 97, no. 20, pp. 10654-10959, 2000; Jeyakumar et al., Ann. Neurol., vol. 56, no. 5, pp. 642-649, 2004).

Example 4

Imaging Neurodegeneration

[$^{125}$I]-IodoDPA713 microSPECT/CT for Dynamic In Vivo Imaging of TSPO.

An X-SPECT small-animal SPECT/CT system (Gamma Medica-Ideas) was used for image acquisition. Each mouse was anesthetized with isofluorane prior to imaging. About 1-2 mCi of [$^{125}$I]-IodoDPA713 was injected into each mouse via intravenous injection, and images were acquired immediately after injection. The SPECT projection data were acquired using 2 low-energy, high-resolution parallel-hole collimators with a radius of rotation of 4.65 cm (spatial resolution, 1.6 mm). The tomographic data were acquired in 64 projections over 360° at 20 s per projection. After tomography, CT was acquired in 512 projections to allow anatomic coregistration. Data were reconstructed using the ordered subsets-expectation maximization algorithm and analyzed using AMIDE software (free software provided by SourceForge). Data was analyzed using Analysis software, and time activity curve of the [$^{125}$I]-IodoDPA713 uptake was generated for each mouse. Three mice per genotype were scanned for the study. For the blocking study, non-radioactive IodoDPA713 (20 µM) was intravenously co-injected with [$^{125}$I]-IodoDPA713, and images were acquired immediately after [$^{125}$I] injection.

In Vivo microSPECT Imaging Showed Higher Uptake of [$^{125}$I]-IodoDPA713 in Sandhoff Disease Mice.

Figure 8:
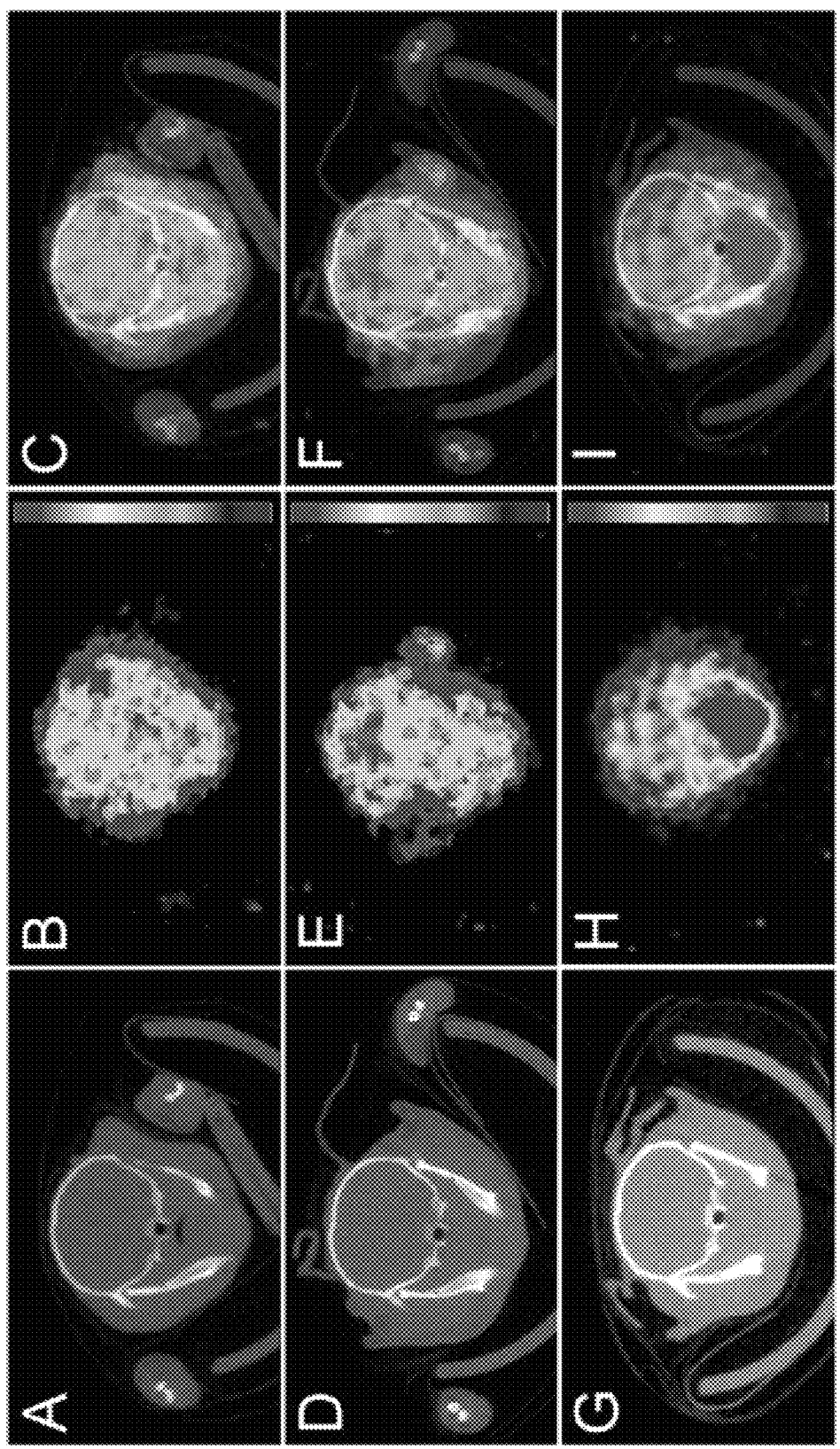
FIG. 8 shows In vivo microSPECT imaging showed higher uptake of [$^{125}$I]-IodoDPA713 in Sandhoff disease mice. Representative mouse brain slices showing [$^{125}$I]IodoDPA-713 accumulation in wildtype (FIGS. 8A-8C), 3-month Sandhoff (FIGS. 8D-8F), and Sandhoff mice (FIGS. 8G-8I) with blocker. The CT, for orientation purposes, indicates that slices (FIGS. 8A, 8D, 8G) are at the level of the thalamus. Tracer uptake appears higher in the brain of the Sandhoff mouse (FIGS. 8E, 8F), and the uptake was blocked by co-injection of non-radiolabeled IodoDPA-713 (FIGS. 8(G, H)).

[$^{125}$I]-IodoDPA713 microSPECT was used to assess TSPO expression in vivo in Sandhoff mice. Co-registered microSPECT images (FIGS. 8B, 8E, 8H) with microCT (FIGS. 8A, 8D, 8G) showed that there is higher uptake of [$^{125}$I]-IodoDPA713 in the Sandhoff mouse (FIG. 8F) compared to wildtype mouse (FIG. 8C). Time-activity curve of the thalamus further showed that Sandhoff mouse consistently had higher uptake of [$^{125}$I]-IodoDPA713 than wildtype mouse (FIG. 8J). Quantitative analysis of the SPECT imaging showed a trend of increased uptake of [$^{125}$I]IodoDPA-713 in the thalamus, cerebellum, and brainstem, and there was a statistically significant increase of [$^{125}$I]-IodoDPA713 uptake in thalamus at 2 months ($t_4=2.81$, $p=0.0484$) and in the brainstem at 3 months ($t_6=3.263$, $p=0.0172$) compared to wildtype (FIG. 8K). A blocking study of a Sandhoff mouse using nonradioactive IodoDPA713 (20 µM) resulted in the reduced uptake of [$^{125}$I]-IodoDPA713 compared to [$^{125}$I]-IodoDPA713 uptake of Sandhoff mouse without blocker (FIG. 8I).

[$^{125}$I]-IodoDPA713 was then used to image TSPO levels in vivo by microSPECT. There is a trend of increased [$^{125}$I]-IodoDPA713 uptake in Sandhoff mice with significant increase in thalamus of 2-month Sandhoff mice and in the brainstem of 3-month Sandhoff mice (FIG. 5K). Furthermore, the time-activity curve indicated that Sandhoff mice consistently had a higher uptake of [$^{125}$I]-IodoDPA713 in the thalamus than wildtype mice (FIG. 5J). A blocking study of a Sandhoff mouse using nonradioactive IodoDPA713 resulted in the reduced uptake of [$^{125}$I]-IodoDPA713 compared to [$^{125}$I]-IodoDPA713 uptake of Sandhoff mouse without blocker (FIG. 5I). This study is important to demonstrate the pharmacological specificity of the tracer uptake. Thus, supporting ex vivo findings of increased TSPO levels in Sandhoff mice with the in vivo imaging study.

Quantitative Receptor Autoradiography.

Fresh-frozen brains were sectioned (20 µm) on a freezing cryostat in the horizontal plane. Brain sections were thaw-mounted onto poly-L-lysine-coated slides (Sigma-Aldrich, St. Louis, Mo.) and stored at −20° C. until used. [$^{125}$I]-IodoDPA713 autoradiography to measure TSPO levels were performed on adjacent brain sections using the same procedures. Slides were thawed and dried at 37° C. for 30 min and prewashed in 50 mM Tris-HCl buffer (pH 7.4) for 5 min at room temperature. Sections were then incubated in 0.5 nM [$^{125}$I]-IodoDPA713 in buffer for 30 min at room temperature. For non-specific binding, adjacent sections were incubated in the presence of 10 mM racemic PK11195. The reaction was terminated by two 3-min washes in cold buffer (4° C.) and two dips in cold deionized water (4° C.). Sections incubated with [$^{125}$I]-IodoDPA713 were apposed to Kodak Bio-Max MR films with [$^{125}$I]-Microscales (GE Healthcare, Piscataway, N.J.) for 1 h. Images were acquired and quantified using the MCID software (InterFocus Imaging Ltd, Cambridge, England).

Longitudinal Assessment of TSPO Levels in Sandhoff Disease Mice Using [$^{125}$I]-IodoDPA713 Quantitative Autoradiography.

Figure 7:
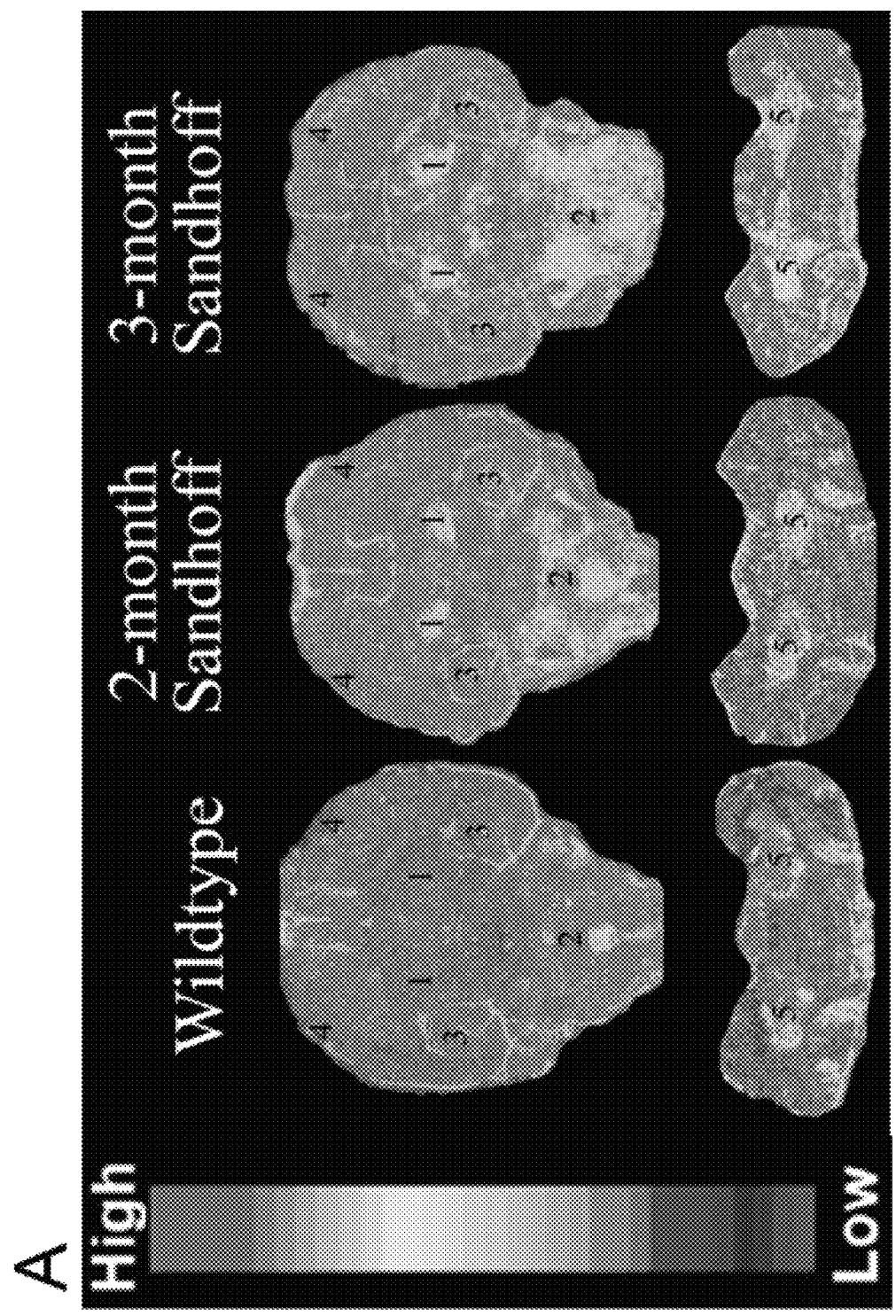
FIG. 7 shows longitudinal assessment of TSPO levels in Sandhoff disease mice using [$^{125}$I]-IodoDPA713 quantitative autoradiography.

Quantitative autoradiography with [$^{125}$I]-IodoDPA713 was used to measure TSPO levels in different brain regions in Sandhoff mice at 2 and 3 months of age. The goal was to assess whether TSPO levels are significantly increased prior to severe expression of disease indicating its potential use as an early biomarker of disease and to assess the expression of TSPO as a function of disease progression. Sandhoff mice expressed increased [$^{125}$I]-IodoDPA713 binding to TSPO in the thalamus, brainstem, and cerebellum, the brain regions known to be affected in Sandhoff mice (Wada et al., Proc. Natl. Acad. Sci. USA, vol. 97, no. 20, pp. 10954-10959, 2000). At 2 months, significant increases of [$^{125}$I]-IodoDPA713 binding to TSPO in the thalamus ($t_8$=5.35, p=0.0007) and in the brainstem ($t_7$=5.28, p=0.0011) of Sandhoff mice (FIG. 7A) were measured. There was a modest increase of [$^{125}$I]-IodoDPA713 binding in the cerebellum, but it did not reach statistical significance ($t_8$=1.871, p=0.098). At 2 months, there was no significant increase in TSPO in the cerebral cortex ($t_6$=0.03, p=0.98) or in the hippocampus ($t_8$=0.49, p=0.63) (FIG. 7B). On the other hand, at 3 months, increased TSPO binding in the thalamus ($t_8$=9.63, p<0.0001) and brainstem ($t_8$=4.69, p=0.0016) was measured; however, at this time point, there was increased binding in the cerebral cortex ($t_6$=4.595, p=0.0037) and cerebellum ($t_7$=3.198, p=0.0151) as well. There was no increased TSPO binding in the hippocampus ($t_8$=0.5594, p=0.5912) at this age (FIG. 7C). These findings clearly show that the temporal expression of TSPO differs according to brain region. These findings are consistent with the known neuropathology of Sandhoff disease (Sango et al., Nature Genetics, vol. 11, no. 2, pp. 170-176, 1995; Wada et al., Proc. Natl. Acad. Sci. USA, vol. 97, no. 20, pp. 10954-10959, 2000), and it also demonstrates the utility of TSPO as an early pre-clinical biomarker of disease.

Silver Staining for Neuronal Degeneration.

Free-floating sections from PFA-perfused animals were further fixed in 4% PFA in 0.1M phosphate buffer for at least 48 h before staining. Silver staining was performed using the FD Neurotech NeuroSilver Kit (Ellicott City, Md.) according to manufacturer's instructions.

Reactive Gliosis Occurs Prior to Neurodegeneration and has a Temporal Response in Sandhoff Disease.

Figure 9:
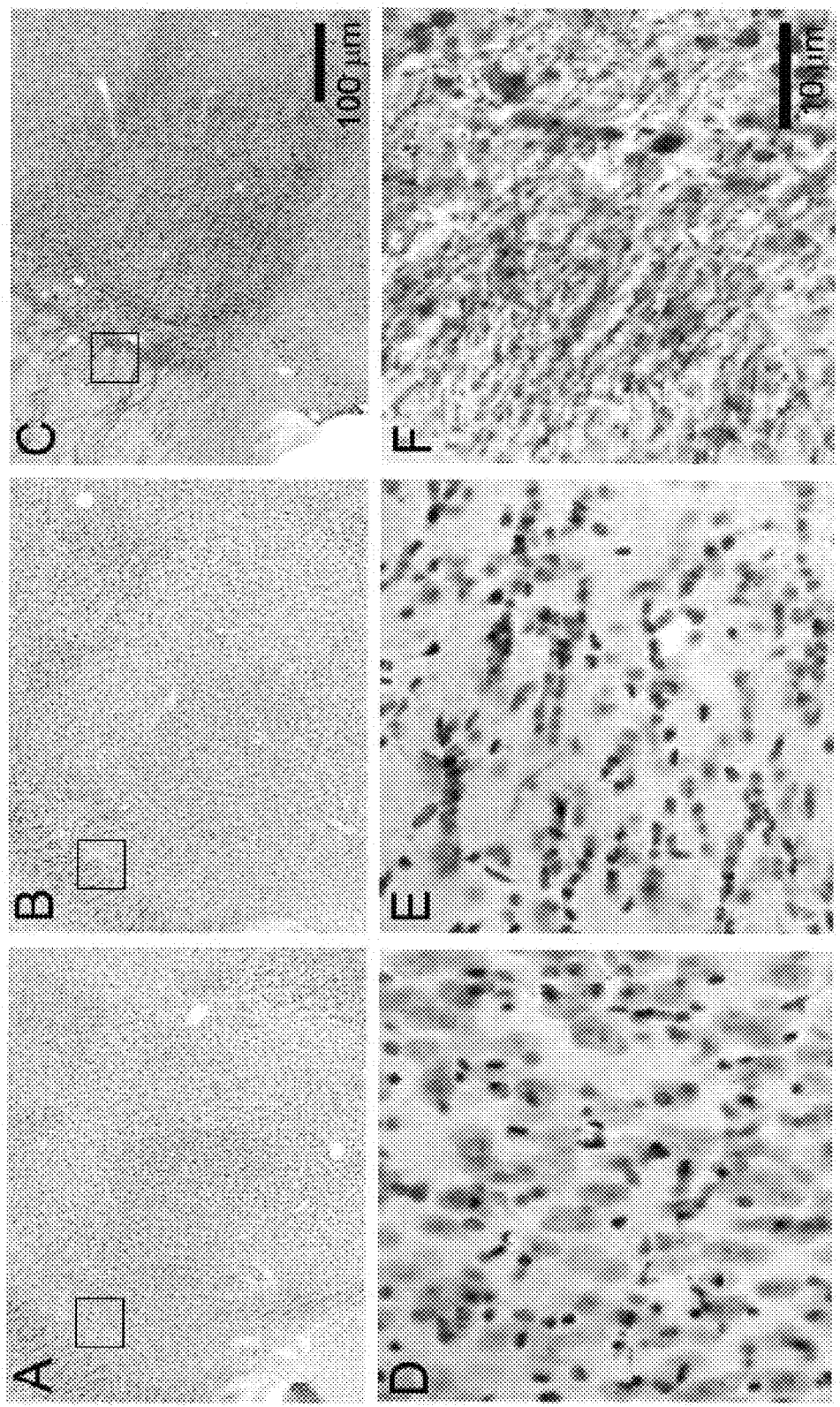
FIG. 9 shows neurodegeneration in Sandhoff disease mice using silver staining. Representative horizontal brain photomicrographs of silver staining indicates ongoing neurodegeneration in the thalamus (FIGS. 9A-9F), cerebellum (FIGS. 9G-9L), and brainstem (FIGS. 9M-9R). Boxes inside the low magnification of thalamus (FIGS. 9A-9C), cerebellum (FIGS. 9G-9I), and brainstem (FIGS. 9M-9O) indicate the area of which the high-magnification images were generated. At 2 months, Sandhoff mice showed no significant silver accumulation in the thalamus (FIGS. 9B, 9E)) and brainstem (FIGS. 9N, 9Q) compared to wildtype (FIGS. 9A and 9D for thalamus; 9M and 9P for brainstem). There was slight silver accumulation in the cerebellum of 2-month Sandhoff mice (FIGS. 9H, 9K)) compared to wildtype (FIGS. 9G, 9J)). At 3 months, Sandhoff mice showed robust silver accumulation in the fiber tracks from the thalamus (FIGS. 9C, 9F) and in the cell bodies of the cerebellum (FIGS. 9I, 9L)) as well as the brainstem (FIGS. 9O, 9R)), indicative of neurodegeneration. For low magnification, scale bar=100 μm. For high magnification, scale bar=10 μm.

Silver staining was used to assess the progression of neurodegeneration in the principal regions known to be affected in Sandhoff disease. These included the thalamus, brainstem, and the cerebellum. 2-month Sandhoff mice did not show any substantial sign of ongoing neurodegeneration in the thalamus (FIGS. 9B, 9E), in the cerebellum (FIGS. 9H, 9K), or in the brainstem (FIGS. 9N, 9Q) compared to wildtype (FIGS. 9A, 9D, 9G, 9J, 9M, 9P). At the thalamus, 2-month Sandhoff mice exhibit little to no silver accumulation (FIGS. 9B, 9E) while 3-month Sandhoff mice exhibited silver accumulation in the fiber tracks of the thalamus (FIGS. 9C, 9F). At the brainstem, 2-month Sandhoff mice exhibited no substantial silver accumulation (FIGS. 9N, 9Q) while 3-month Sandhoff mice exhibited robust silver accumulation (FIGS. 9O, 9R), indicative of neurodegeneration. Finally, at the cerebellum, slight silver accumulation was observed in the cerebellum of 2-month Sandhoff mice (FIGS. 9H, 9K) but robust silver accumulation in cerebellum of 3-month Sandhoff mice (FIGS. 9I, 9L). Consistent with the behavioral data, at 3 months, there were prominent argyrophilic neurons consistent with ongoing neurodegeneration in all examined regions (FIGS. 9C, 9F, 9I, 9L, 9O, 9R).

GFAP and Mac-1 (CD11b) Immunohistochemistry.

Free-floating brain sections from PFA-perfused animals were sectioned (40 µm) using a freezing microtome (Leica Microsystems Inc., Bannockburn, Ill.). Sections were incubated in 0.6% $H_2O_2$ for 15 min followed by blocking solution with either 5% normal goat serum containing 0.2% Triton X-100 for 1 h. Sections were incubated with rabbit anti-GFAP antibody (1:1000, Dako, Carpinteria, Calif., USA) or rat anti-mouse CD11b antibody (1:250, BD PharMingen, San Diego, Calif., USA) at 4° C. overnight. Sections were then incubated with biotinylated goat anti-rabbit antibody for GFAP (1:200, Vector, Burlingame, Calif.) or biotinylated rabbit anti-rat antibody for Mac-1 (1:200, Vector) for 1 h. Immunoreactivity was visualized using ABC elite, an avidin-biotin-horseradish peroxidase (HRP) complex (Vector), with 3,3'-diaminobenzidine (DAB) (Sigma) as the chromogen.

To assess the progression of microglia and astrocyte activation, Mac-1 and GFAP immunohistochemistry were used to detect microglia and astrocytes, respectively. Increased Mac-1 immunoreactivity was observed at 2-month but a more robust Mac-1 immunoreactivity at 3-month. The microglia also appeared hypertrophic in the brainstem at 3-month compared to wildtype. Similarly, 3-month Sandhoff mice showed higher GFAP immunoreactivity than 2-month Sandhoff mice. While 2-month Sandhoff mice exhibited activated microglia and astrocyte, both responses appeared stronger in the cerebellum of 3-month Sandhoff mice.

Figure 10:
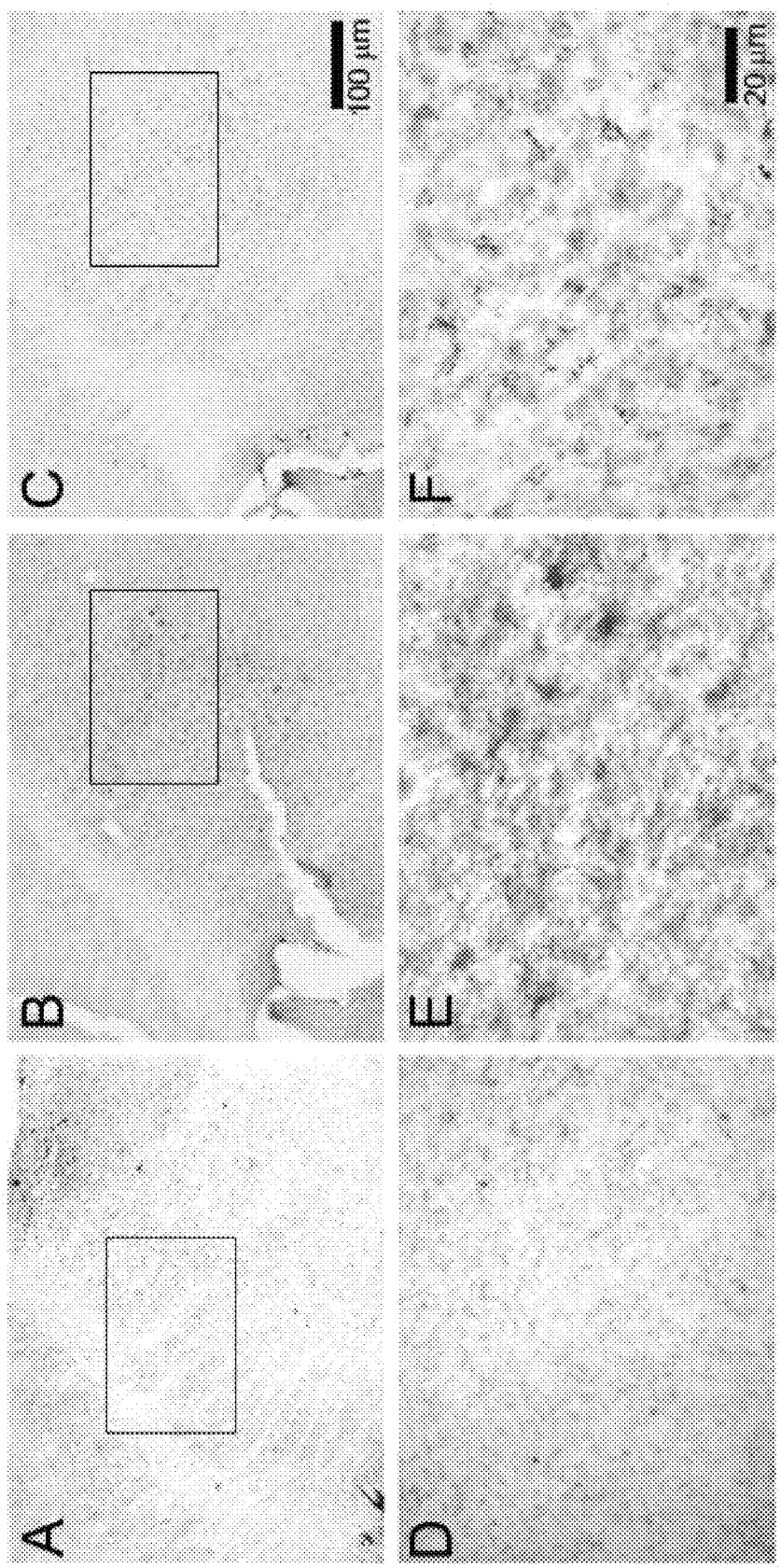
FIG. 10 shows regional and temporal expression of microglia activation using CD11b immunohistochemistry. Representative horizontal brain micrographs of CD11b, a microglia specific marker, in Sandhoff mice at the level of thalamus (FIGS. 10A-10F), cerebellum (FIGS. 10G-10L), and brainstem (FIGS. 10M-10R). Boxes inside the low magnification of thalamus (FIGS. 10A-10C), cerebellum (FIGS. 10G-10I), and brainstem (FIGS. 10M-10O) indicate the area of which the high-magnification images were generated. Wildtype mice (FIGS. 10A, 10D, 10G, 10J, 10M, 10P) exhibited little to no detection of activated microglia. In the thalamus, 2-month Sandhoff mice (FIGS. 10B, 10E) appeared to exhibit higher CD11b labeling than 3-month Sandhoff mice (FIGS. 10C, 10F) and wildtype (FIGS. 10A, 10D). In the cerebellum, both 2-month (FIGS. 10H, 10K) and 3-month (FIGS. 10I, 10L) Sandhoff mice exhibited increased CD11b labeling compared to wildtype (FIGS. 10G, 10J). In the brainstem, 3-month Sandhoff mice (FIGS. 10O, 10R) appeared to exhibit higher CD11b labeling than 2-month Sandhoff mice (FIGS. 10N, 10Q) and wildtype (FIGS. 10M, 10P)). For low magnification, scale bar=100 μm. For high magnification, scale bar=20 μm.
Figure 11:
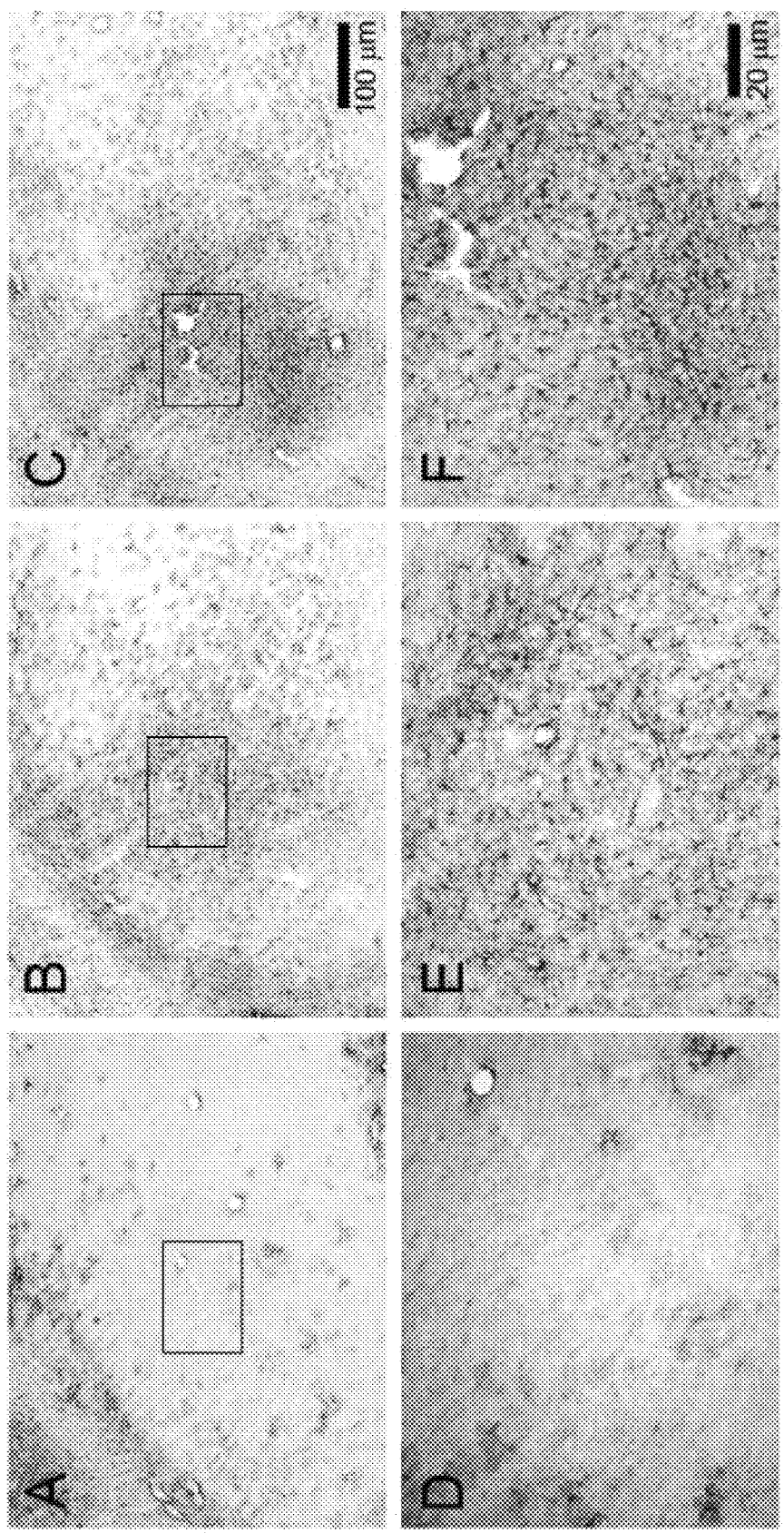
FIG. 11 shows temporal response of astrocyte activation in Sandhoff disease mice. Representative horizontal brain micrographs of GFAP, an astrocyte specific marker, in Sandhoff mice at the level of thalamus (FIGS. 11A-11F), cerebellum (FIGS. 11G-11L), and brainstem (FIGS. 11M-11R). Boxes inside the low magnification of thalamus (FIGS. 11A-11C), cerebellum (FIGS. 11G-11I), and brainstem (FIGS. 11M-11O) indicate the area of which the high-magnification images were generated. Wildtype mice (FIGS. 11A, 11D, 11G, 11J, 11M, 11P) exhibited little detection of activated astrocytes. In all regions, activated astrocytes were seen at 2-month Sandhoff mice (FIGS. 11B, 11E, 11H, 11K, 11N, 11Q) but were more pronounced at 3 months Sandhoff mice (FIGS. 11C, 11F, 11I, 11L, 11O, 11R). For low magnification, scale bar=100 μm. For high magnification, scale bar=20 μm.

In the thalamus, more activated microglia were seen in 2-month Sandhoff mice (FIGS. 10B, 10E) than in 3-month Sandhoff mice (FIGS. 10C, 10F). Meanwhile, activated astrocytes appeared higher in the thalamus of 3-month Sandhoff mice (FIGS. 11C, 11F) than 2-month Sandhoff mice (FIGS. 11B, 11E). In the cerebellum, more activated microglia and astrocytes were detected at 3-month Sandhoff mice (FIGS. 10I, 10L for microglia; FIGS. 11I, 11L for astrocytes) for than 2-month Sandhoff mice (FIGS. 10H, 10K for microglia; FIGS. 11H, 11K for astrocytes) and wildtype (FIGS. 10G, 10J for microglia; FIGS. 11G, 11J for astrocytes). Similarly, in the brainstem, more activated microglia and astrocytes were detected at 3-month Sandhoff mice (FIGS. 10O, 10R for microglia; FIGS. 11O, 11R for astrocytes) for than 2-month Sandhoff mice (FIGS. 10N, 10Q for microglia; FIGS. 11N, 11Q for astrocytes) and wildtype (FIGS. 10M, 10P for microglia; FIGS. 11M, 11P for astrocytes). This suggests that there is a regional and temporal response in reactive gliosis demonstrating microglial activation preceding astrocyte activation.

Increased Mac-1 immunoreactivity was observed at 2-month but a more robust Mac-1 immunoreactivity at 3-month. The microglia also appeared hypertrophic in the brainstem at 3-month compared to wildtype. Similarly, 3-month Sandhoff mice showed higher GFAP immunoreactivity than 2-month Sandhoff mice. While 2-month Sandhoff mice exhibited activated microglia and astrocyte, both responses appeared stronger in the cerebellum of 3-month Sandhoff mice.

Double Labeling of GFAP or Mac-1 Immunohistochemistry and High-Resolution [$^3$H]-(R)-PK11195 Emulsion Autoradiography.

PLP-perfused brain tissue was used to determine the co-localization of TSPO with microglia or astrocytes. It has been shown that there are no differences in [³H]-(R)-PK11195 binding to TSPO between fresh-frozen and PLP-fixed brain tissue (Kuhlmann et al. Toxicol. Sci., vol. 48, no. 1, pp. 107-116, 1999). PLP-fixed brains were sectioned (18 μm) on a freezing cryostat in the horizontal plane. Brain sections were thaw-mounted onto poly-L-lysine-coated slides and stored at −20° C. until used. Immunohistochemistry of GFAP or Mac-1 was performed as described above. After processing of the DAB stain, slides were immediately processed for [³H]-(R)-PK11195 (1.5 nM concentration) receptor autoradiography performed as described above. Tissue sections were air-dried, coated with photographic hypercoat emulsion (EM-1; GE Healthcare Bio-Sciences Corporation, Piscataway, N.J.) and exposed in the dark for 4 weeks. Kodak D-19 developer and 30% (weight per volume) sodium thiosulfate as fixer were used for photographic processing.

Increased TSPO Binding is Co-Localized in Activated Microglia and Astrocytes.

High-resolution emulsion autoradiography of [³H]-(R)-PK11195 binding to TSPO was performed to determine the cellular localization of increased TSPO binding in Sandhoff mice. The silver grain density represents the levels of [³H]-(R)-PK11195 binding to TSPO. Similar to receptor autoradiography, Sandhoff mice showed higher [³H]-(R)-PK11195 binding in the thalamus (FIGS. 12B and 13B), cerebellum (FIGS. 12E and 13E), and brainstem (FIGS. 12H and 13H) compared to wildtype (FIGS. 12A, 12D, 12G and FIGS. 13A, 13D, 13G). Combined with GFAP or Mac-1 immunohistochemistry, [³H]-(R)-PK11195 binding to TSPO appeared to occur in both activated microglia and astrocytes in all 3 regions (FIGS. 12B, 12E, 12H and FIGS. 13B, 13E, 13H). This binding is specific as nonradioactive PK11195 was able to compete with [³H]-(R)-PK11195 binding (FIGS. 12C, 12F, 12I and FIGS. 13C, 13F, 13I). These images confirm the increased TSPO binding in brain regions affected in the Sandhoff mice is associated with the reactive gliosis response with activated microglia and astrocytes.

Because increased TSPO expression during brain injury and inflammation is primarily found in microglia and astrocytes as a prominent component of reactive gliosis, the response of microglia and astrocytes in Sandhoff disease and wildtype mice at 2 and 3 months of age by Mac-1 and GFAP immunostaining, respectively were measured. Interestingly, prior to severe neurodegeneration, 2-month Sandhoff mice exhibited microglia activation in the thalamus, characterized by increased Mac-1 immunohistochemical staining (FIG. 10). The microglia appeared to be activated as they looked hypertrophic, a consistent morphological characteristic of microglial activation in vivo. The microglia response in the thalamus appears to be maximal at 2 months since immunostaining of 3-month Sandhoff mice exhibited a reduced level of microglia staining in the thalamus (FIGS. 10C, 10F). Both 2- and 3-month Sandhoff mice exhibited enhanced astrocytic response in the thalamus as shown by the increased GFAP immunoreactivity relative to wildtype mice (FIG. 11A-11F). An increased Mac-1 immunoreactivity at 2-month but a more robust Mac-1 immunoreactivity at 3-month was observed. The microglia also appeared hypertrophic in the brainstem at 3-month compared to wildtype. Similarly, 3-month Sandhoff mice showed higher GFAP immunoreactivity than 2-month Sandhoff mice.

Statistical Analysis.

Repeated measure analysis of variance (ANOVA) was used for comparison of weekly body weights and locomotor activity between wildtype and Sandhoff mice. For rotarod test, quantitative autoradiography, and SPECT imaging, student's t-test was used for comparison between wildtype and Sandhoff mice. For all tests, the significance level was set at $p<0.05$.

CONCLUSION

There was shown a regional and temporal response of reactive gliosis in Sandhoff disease Sandhoff mice that occurs prior to neurodegeneration. While little to no neurodegeneration was observed during 2 months of age, an increased number of activated microglia were observed in the thalamus of 2-month Sandhoff mice. These findings are consistent with an earlier study where reactive gliosis was seen prior to neurodegeneration (Veiga et al. Glia, vol. 55, no. 14, pp. 1426-1436, 2007). Neurodegeneration was seen at 3 months as there were prominent silver accumulation at the brainstem, thalamus, and cerebellum. Moreover, the reactive gliosis response appeared to shift both regionally and temporally as at 3 months, Sandhoff mice showed higher microglia activation in the brainstem and cerebellum than at 2 months, and astrocyte activation at all 3 regions appeared more prominent as well.

As aforementioned, in the thalamus, TSPO levels remained elevated at both time points, but an increase of activated microglia at 2 months and an increase of activated astrocytes at 3 months was observed. This might be a result of the shift of TSPO expression from microglia to astrocytes as reactive gliosis persists in Sandhoff disease. Previous studies have also shown this similar temporal response of TSPO expression, which was first associated with microglia activation and then followed by TSPO associated with astrocytosis (Kuhlmann et al., J. Neurochem., vol. 74, no. 4, pp. 1694-1704, 2000; Chen et al., Brain, vol. 127, no. 6, pp. 1379-1392, 2004). While it is known that increased TSPO is localized primarily in glial cells, a colocalization study is required to confirm that the increased TSPO binding is indeed localized in glial cells and to establish which cell type expresses TSPO.

As shown below, in vivo [¹²⁵I]-IodoDPA-713 microSPECT imaging of the brain, and in vivo [¹²⁵I]-IodoDPA-713 microSPECT imaging also showed increased uptake of [¹²⁵I]-IodoDPA-713 in Sandhoff mice at both time points. Several conclusions can be drawn from this study. [¹²⁵I]-IodoDPA-713 is an attractive radioligand for TSPO imaging using SPECT, and secondly, TSPO is a sensitive biomarker of brain injury such that increased TSPO binding can be detected prior to demonstration of behavioral changes and significant levels of neurodegeneration. Finally, the use of [¹²⁵I]-IodoDPA-713 autoradiography compared to using tritium-labeled TSPO ligands has the advantage that the autoradiography images can be obtained in a relative short amount of time (2-6 h) while tritium-labeled ligands requires a minimum of 4-6 weeks.

Several reports have shown the use of in vivo TSPO imaging in various models of brain injuries in rodents as well as human neurological disorders (Chen et al., Toxicol. Sci., vol. 91, no. 2, pp. 532-539, 2006; Gerhard et al., Neuroreport., vol. 11 no. 13, pp. 2957-2960, 2000; Gerhard et al., NeuroImage, vol. 24, no. 2, pp. 591-595, 2005; Pappata et al. Neurology, vol. 55, no. 7, pp. 1052-1054, 2000; Price et al., Stroke, vol. 37, no. 7, pp. 1749-1750, 2006; Miyazawa et al., Acta Neurochir., vol. 137, no. 3-4, pp. 207-16, 1995; Raghavendra et al., Exp. Neurol., vol. 161, no. 1, pp. 102-114, 2000; Cagnin et al., Neurotherapeutics, vol. 4, pp. 443-452, 2007; Versijpt et al., Eur. Neurol., vol. 50, no. 1, pp. 39-47, 2003; Ouchi et al., Ann. Neurol., vol. 57, no. 2, pp. 168-175, 2005; Gerhard et al., Neurobiol. Dis., vol. 21, no. 2, pp. 404-412, 2006). However, most of these reports were cross-sectional in nature. The current study clearly shows that increased TSPO levels were increased in several brain regions from Sandhoff mice prior to severe behavioral manifestation of disease. Thus, TSPO can be used as an early biomarker of neurodegeneration.

In summary, this study examined TSPO binding longitudinally using Sandhoff disease Sandhoff mice at time points prior to and during neurodegeneration. Using a novel TSPO ligand [$^{125}$I]-IodoDPA-713, TSPO binding was detected in specific regions both in vitro and in vivo at the time points prior to and during neurodegeneration as well as an increased glial response marked by microglia and astrocyte activation. The glial response also appeared to be regional and temporal as microglia activation was detected at an earlier time point before astrocyte activation. These findings suggest the use of TSPO as a pre-clinical marker of brain injury to track the progression of injury over time.

In this study, [$^{125}$I]-IodoDPA713 was used to assess the progression of TSPO expression of Sandhoff disease mouse model in a longitudinal fashion. TSPO levels were visualized and measured using both in vitro quantitative autoradiography and in vivo imaging using microSPECT at 2 months and at 3 months of age. It was found that at 2 months, when Sandhoff disease mice show slight deficits in behavioral endpoints and without severe neurodegeneration as measured by silver staining, increased TSPO expression was detected in brain regions known to undergo neurodegeneration in Sandhoff disease mice. This increase in TSPO binding appeared to co-localize with activated microglia and astrocytes. In the thalamus, 2-month Sandhoff disease mice showed higher activation of microglia than astrocytes, and previous studies demonstrated that the early TSPO response appeared to be associated with microglia activation and not with astrocytosis. On the other hand, at 3 months when Sandhoff disease mice showed significant motor deficits and neurodegeneration, the increase of TSPO levels at the thalamus, brainstem, and cerebellum was associated with both activated microglia and astrocytes. This study is the first to use a new and improved ligand for TSPO to assess the longitudinal expression of TSPO and neurodegeneration in a mouse model of Sandhoff disease.

Example 5

Dynamic Imaging in Heart

[$^{125}$I]-IodoDPA713 microSPECT/CT for Dynamic In Vivo Imaging of TSPO.

An X-SPECT small-animal SPECT/CT system (Gamma Medica-Ideas) was used for image acquisition. Each mouse was anesthetized with isofluorane prior to imaging. About 1-2 mCi of [$^{125}$I]-IodoDPA713 was injected into each mouse via intravenous injection, and images were acquired immediately after injection. The SPECT projection data were acquired using 2 low-energy, high-resolution parallel-hole collimators with a radius of rotation of 4.65 cm (spatial resolution, 1.6 mm). The tomographic data were acquired in 64 projections over 360° at 20 s per projection. After tomography, CT was acquired in 512 projections to allow anatomic coregistration. Data were reconstructed using the ordered subsets-expectation maximization algorithm and analyzed using AMIDE software (free software provided by SourceForge). Data was analyzed using Analysis software, and time activity curve of the [$^{125}$I]-IodoDPA713 uptake was generated for each mouse. Three mice per treatment were scanned for the study.

FIG. 14 shows representative transverse slices showing the difference of [$^{125}$I]IodoDPA-713 accumulation between PBS-injected control mouse (top panel) and coxsackievirus-injected mouse (bottom panel). The CT (left), for orientation purposes, indicates that slices are at the level of the heart (solid line). Tracer uptake appears higher in the heart of coxsackievirus-injected mouse than the control mouse. FIG. 15 shows quantitative analysis of tracer uptake showed that coxsackievirus-injected mice showed a statistically significant increase of [$^{125}$I]-IodoDPA713 uptake than the PBS-injected control mice. The tracer uptake in the lungs and liver were also analyzed to indicate that the increased [$^{125}$I]-IodoDPA-713 uptake is heart-specific. Images are expressed in units of standardized uptake values (SUV) and are normalized for weight and injected dose. Data is expressed as the mean of SUV±SEM (n=3 male mice per group, *p<0.05 compared to control using a paired t-test).

As described herein, all embodiments or subcombinations may be used in combination with all other embodiments or subcombinations, unless mutually exclusive.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A compound having the structure

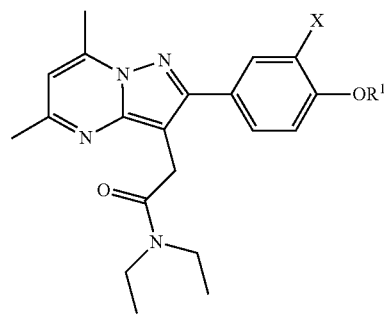

wherein X is I, $^{123}$I, $^{124}$I, $^{125}$I, or $^{131}$I, and R$^1$ is H or CH$_3$.

2. The compound according to claim 1 having the structure

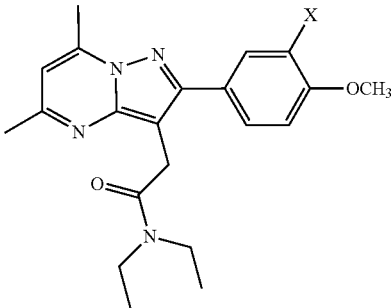

where X is I, $^{123}$I, $^{124}$I, $^{125}$I, or $^{131}$I.

3. The compound according to claim 2, where the compound is isotopically enriched in one of $^{123}$I, $^{124}$I, $^{125}$I, or $^{131}$I.

4. A method for imaging cells, a sample, an organ or a subject comprising imaging cells, a sample, an organ or a subject with increased levels of translocator protein, TSPO, after administration of a detectably sufficient amount of a radioisotopically-enriched compound according to claim 2.

5. The method of claim 4, further comprising administering a detectably sufficient amount of a radioisotopically-enriched compound according to claim 2 before said imaging.

6. The method according to claim 4 wherein said imaging is autoradiography.

7. The method according to claim 4 wherein said imaging is single photon emission computed tomography and the compound is radioisotopically-enriched with $^{123}$I or $^{125}$I.

8. The method according to claim 4 wherein said imaging is positron emission tomography and the compound is radioisotopically-enriched with $^{124}$I.

9. The method according to claim 4 wherein cells are glial cells or immune cells.

10. The method according to claim 4, wherein the organ is the brain.

11. The method according to claim 4, wherein the organ is the lungs.

12. The method according to claim 4, wherein the organ is the heart.

13. The method according to claim 4, wherein the subject has inflammation.

14. The method according to claim 4, wherein the subject has an autoimmune disease.

15. The method according to claim 4, wherein the subject has inflammatory arthritides.

16. The method according to claim 4, wherein the subject has a neurodegenerative disease.

17. The method according to claim 4, wherein the subject has atherosclerosis.

* * * * *